US012691066B2

(12) United States Patent
Xie et al.

(10) Patent No.: US 12,691,066 B2
(45) Date of Patent: Jul. 28, 2026

(54) DUAL-TARGETING BIOMIMETIC LIPOSOME WITH ELEMENE (ELE) AND CABAZITAXEL (CTX), AND PREPARATION METHOD AND USE THEREOF

(71) Applicant: HANGZHOU NORMAL UNIVERSITY, Hangzhou (CN)

(72) Inventors: Tian Xie, Hangzhou (CN); Yiying Zeng, Hangzhou (CN); Jie Li, Hangzhou (CN); Zhaowu Zeng, Hangzhou (CN)

(73) Assignee: HANGZHOU NORMAL UNIVERSITY, Hangzhou (CN)

( * ) Notice: Subject to any disclaimer, the term of this patent is extended or adjusted under 35 U.S.C. 154(b) by 205 days.

(21) Appl. No.: 18/591,795

(22) Filed: Feb. 29, 2024

(65) Prior Publication Data

US 2024/0252436 A1     Aug. 1, 2024

Related U.S. Application Data

(63) Continuation-in-part of application No. PCT/CN2022/115489, filed on Aug. 29, 2022.

(30) Foreign Application Priority Data

Aug. 30, 2021     (CN) .......................... 202111003702.1

(51) Int. Cl.
| | |
|---|---|
| *A61K 9/1271* | (2025.01) |
| *A61K 31/015* | (2006.01) |
| *A61K 31/337* | (2006.01) |
| *A61K 47/10* | (2017.01) |
| *A61K 47/24* | (2006.01) |
| *A61K 47/42* | (2017.01) |
| *A61P 35/00* | (2006.01) |

(52) U.S. Cl.
CPC .......... *A61K 9/1271* (2013.01); *A61K 31/015* (2013.01); *A61K 31/337* (2013.01); *A61K 47/10* (2013.01); *A61K 47/24* (2013.01); *A61K 47/42* (2013.01); *A61P 35/00* (2018.01)

(58) Field of Classification Search
CPC .... A61K 9/1271; A61K 31/015; A61K 47/10; A61K 47/24; A61K 47/42; A61P 35/00
See application file for complete search history.

(56) References Cited

U.S. PATENT DOCUMENTS

2013/0058873 A1     3/2013   Jefferies et al.

FOREIGN PATENT DOCUMENTS

| | | | |
|---|---|---|---|
| CN | 101921164 A | 12/2010 | |
| CN | 109260156 A | * 1/2019 | ............. A61K 47/28 |
| CN | 111888331 A | 11/2020 | |
| CN | 113768878 A | 12/2021 | |

OTHER PUBLICATIONS

Ishida (Pharmaceutical Research, vol. 18, No. 7, 2001, pp. 1042-1048). (Year: 2001).*
Li, Jie, et al., "Active targeting of orthotopic glioma using biomimetic liposomes co-loaded elemene and cabazitaxel modified by transferrin", Journal of Nanobiotechnology, vol. 19, No. 1. Sep. 26, 2021, Paper No. 289, https://doi.org/10.1186/s12951-021-01048-3.
Ferraris. C. et al. "Overcoming the Blood-Brain Barrier: Successes and Challenges in Developing Nanoparticle-Mediated Drug Delivery Systems for the Treatment of Brain Tumours." International Journal of Nanomedicine, Dovepress, vol. 15, Apr. 30, 2020, pp. 2999-3022, https://doi.org/10.2147/IJN.S231479.

* cited by examiner

*Primary Examiner* — Alma Pipic
(74) *Attorney, Agent, or Firm* — Jacob M. Ward; Ward Law Office LLC

(57) ABSTRACT

The present disclosure provides a dual-targeting biomimetic liposome with elemene (ELE) and cabazitaxel (CTX), where each 100 mL of the dual-targeting biomimetic liposome with ELE and CTX includes 0.15 g to 0.75 g of the ELE, 0.5 mL to 2.5 mL of absolute ethanol, 0.015 g to 0.07 g of the CTX, 0.25 g to 1 g of oil, 0.25 g to 1 g of a polyethylene glycol (PEG) derivative, 1 g to 5 g of a phospholipid, 0.05 g to 0.2 g of cholesterol, 0.025 g to 0.1 g of distearoyl phosphatidylethanolamine-polyethylene glycol 2000-transferrin (DSPE-PEG2000-Tf), 0.005 g to 0.025 g of a tumor cell membrane protein (CMP), and water as a balance.

8 Claims, 28 Drawing Sheets

(B)

(C)

(E)

(F)

ELE/CTX@BLIP

Tf-ELE/CTX@LIP

Tf-ELE/CTX@BLIP

DUAL-TARGETING BIOMIMETIC LIPOSOME WITH ELEMENE (ELE) AND CABAZITAXEL (CTX), AND PREPARATION METHOD AND USE THEREOF

CROSS-REFERENCE TO RELATED APPLICATIONS

This application is a continuation-in-part of International Patent Application No. PCT/CN2022/115489, filed on Aug. 29, 2022, which claims priority to the Chinese Patent Application No. 202111003702.1, filed with the China National Intellectual Property Administration on Aug. 30, 2021, and entitled "DUAL-TARGETING BIOMIMETIC LIPOSOME WITH ELEMENE (ELE) AND CABAZI-TAXEL (CTX), AND PREPARATION METHOD AND USE THEREOF". The entire disclosures of the above applications are incorporated herein by reference.

FIELD

The present disclosure relates to the technical field of tumor chemotherapy drugs, and in particular to a dual-targeting biomimetic liposome with elemene (ELE) and cabazitaxel (CTX) and a preparation method thereof.

INTRODUCTION

This section provides background information related to the present disclosure which is not necessarily prior art.

Glioma is one of the most threatening diseases to humans, with extremely poor prognosis and high mortality. So far, surgery is the most direct and effective treatment strategy that can significantly reduce symptoms and prolong the survival of glioma patients. However, due to the heterogeneous and infiltrative characteristics, the surgery cannot completely remove glioma and carries a high risk of recurrence. Chemotherapy is also necessary, but the chemotherapy for glioma is generally hampered by the selective permeability of blood-brain barrier (BBB) and the poor drug targeting to tumor tissues. The BBB carries an adenosine triphosphate (ATP)-dependent efflux pump P-glycoprotein (P-gp), which can actively pump out substrates and increase the clearance of cytotoxic drugs. In particular, it is difficult for anticancer drugs to target the glioma area and adsorb to other normal areas after crossing the BBB, and may reduce efficacy or even cause neurotoxicity. Therefore, it is crucial to design a carrier that can penetrate the BBB, escape the efflux mechanism, and target into the glioma.

Liposomes are spherical vesicles formed by a phospholipid bilayer membrane that have attracted widespread attention in terms of biocompatibility and BBB crossing. Liposomes are regarded as a common carrier for neuroglioma treatment. The lack of active targeting and tumor targeting capacities limits the application of liposomes in glioma chemotherapy. There is overexpression of various insulin receptors, transferrin (Tf), endothelial growth factors, and amino acids on the BBB. Receptor-mediated endocytosis is one of the main mechanisms by which various drugs pass through the BBB. Here, the Tf is used as a targeting ligand to modify liposomes to increase BBB penetration through specific recognition of Tf receptors. Although drug accumulation in the brain can be improved by the above methods, targeting glioma after penetrating the BBB remains challenging.

In order to further improve the tumor aggregation of anticancer drugs, biomimetic liposomes are developed by embedding glioma cell membrane proteins (CMPs) into Tf liposomes. In recent years, biomimetic nanoengineering based on cancer cell membranes (proteins) has attracted much attention and is applied to the development of biomimetic liposomes with homologous targeting and immune evasion functions. Liposomes have achieved desirable active targeting due to their specific homotypic binding to the cell membrane of source cancer cells. Furthermore, the immune system has difficulty recognizing membrane-camouflaged liposomes since these liposomes are viewed as cells of origin with long circulation. Since the first report in 2014, CMP-based biomimetic nanoengineering has been widely used in biomedical fields such as immunotherapy, bioimaging, therapeutics, and glioma phototherapy. However, active targeting biomimetic liposomes are rarely reported for glioma chemotherapy.

Cabazitaxel (CTX), a new type of semi-synthetic taxane compound, has a molecular formula of $C45H57NO14$ and a molecular weight of 835.94, and is almost insoluble in water but soluble in ethanol. Preclinical animal studies have shown that the CTX has a broad-spectrum anti-tumor activity on tumors including prostate cancer, colon cancer, lung cancer, and breast cancer, and can cross the BBB. Compared with other paclitaxel drugs, the CTX has a significant inhibitory effect on glioma, but is more toxic. Elemene (ELE) as a natural anti-cancer active ingredient with desirable efficacy and few side effects is extracted and isolated from Curcuma wenyujin Y. H. Chen & C. Ling. The ELE includes various ELE isomers such as $\alpha$, $\beta$, $\gamma$, and $\delta$ types. Studies have found that ELE can produce inhibitory and killing effects on a variety of cancer cells, induce tumor cell differentiation and apoptosis, inhibit tumor cell infiltration and distant metastasis, inhibit tumor angiogenesis, and improve anti-tumor immune responses in vivo. For example, patent CN101921164A "Synthesis and use of (−)-β-elemene, (−)-β-elemarin, (−)-β-elemol, and (−)-β-fluorinated elemene and analogs, intermediates, and compositions thereof" disclosed use of the ELE for cancer, especially for brain tumors, lung cancer, ovarian cancer, bladder cancer, cervical cancer, colon cancer, breast cancer, and prostate cancer with efficacy. The ELE is a fat-soluble small molecule compound that can pass through the BBB and has a certain therapeutic effect on malignant glioma in clinical applications.

SUMMARY

In concordance with the instant disclosure, a dual-targeting biomimetic liposome with ELE and CTX, has surprisingly been discovered.

The present technology includes articles of manufacture and processes that relate to a dual-targeting biomimetic liposome with ELE and CTX.

In order to overcome the problems of high toxicity and low targeting efficiency of CTX when used to treat glioma, the present disclosure provides a dual-targeting biomimetic liposome with ELE and CTX. In the present disclosure, the ELE, the CTX, distearoyl phosphatidylethanolamine-polyethylene glycol 2000-transferrin (DSPE-PEG2000-Tf), CMP, and D-α-tocopherol polyethylene glycol succinate (TPGS) are simultaneously encapsulated in liposomes. This process enables the above two drugs to act synergistically on brain glioma cells, improves a BBB permeability of the drugs and an uptake rate of glioma cells, thus significantly enhancing a targeted efficacy. Meanwhile, the present disclosure significantly reduces the toxic and side effects of CTX and the irritation of ELE, significantly improves safety, and effectively avoids the side effects of the drug on normal brain cells and other tissues and organs. The present disclosure further provides a preparation method of the dual-targeting biomimetic liposome with ELE and CTX.

To achieve the above objective, the present disclosure adopts the following technical solutions:

The present disclosure provides a dual-targeting biomimetic liposome with ELE and CTX, where each 100 mL of the dual-targeting biomimetic liposome with ELE and CTX includes 0.15 g to 0.75 g of the ELE, 0.5 mL to 2.5 mL of absolute ethanol, 0.015 g to 0.07 g of the CTX, 0.25 g to 1 g of oil, 0.25 g to 1 g of a polyethylene glycol (PEG) derivative, 1 g to 5 g of a phospholipid, 0.05 g to 0.2 g of cholesterol, 0.025 g to 0.1 g of distearoyl phosphatidylethanolamine-polyethylene glycol-transferrin (DSPE-PEG-Tf), 0.005 g to 0.025 g of a tumor cell membrane protein (CMP), and water as a balance.

The main reasons that limit the treatment of brain tumors include P-gp pump efflux, drug targeting, and central nervous system toxicity. Accordingly, it is a highly important issue to improve drugs, prevent P-gp pump efflux, enhance tumor targeting, and improve safety. In the present disclosure, the Tf can specifically recognize Tf receptors overexpressed on the BBB; the PEG derivative such as TPGS and the Tf can competitively inhibit substrate binding and inhibit the ATPase of P-gp; the CMP can homologously target tumor cells, increase the cellular uptake rate of drugs, and improve the anti-tumor effect of drugs.

CTX is a new type of taxane anti-tumor drug that is structurally similar to docetaxel and is a product of methoxylation of 7,10-OH of docetaxel. The CTX mainly inhibits tumor cell growth by inducing an increase in mitosis, thus prolonging abnormal mitotic block, promoting tubulin assembly, inhibiting tubulin depolymerization, and destroying tumor cell division. The CTX has a strong inhibitory effect on the cell cycle pathway, and acts on an M phase of cells to block the mitosis of tumor cells and promote their apoptosis. Due to its structural methoxylation, CTX has a weaker affinity for P-glycoprotein than that of paclitaxel and docetaxel, and therefore has a stronger inhibitory effect on drug-resistant tumor cells. However, due to the poor water solubility of CTX, a commercially available preparation Jevtana is added with large amounts of polysorbate 80 and absolute ethanol as co-solvents, resulting in severe side effects such as generalized rash/erythema, hypotension, and bronchospasm.

ELE can pass through the BBB since the ELE is a small fat-soluble molecule (with a molecular weight of 204.3); the ELE further affects the biological pathways of cells by affecting exosome-mediating RNAS to allow intercellular information transmission; the ELE induces apoptosis of tumor cells by downregulating the membrane potential of mitochondria; the ELE induces changes in cell permeability to enhance drug accumulation within cells. The ELE in the present disclosure can be one or more selected from the group consisting of α-ELE, β-ELE, γ-ELE, and δ-ELE.

The ELE and CTX are combined to form a dual-targeting biomimetic liposome, which can exert synergistic effects on multiple targets and multiple pathways, thus exerting joint synergy and preventing drug resistance. At the same time, since CTX is highly toxic while ELE is relatively safe, a dosage of the CTX can be greatly reduced while ensuring the efficacy. ELE is still somewhat irritating, so encapsulating ELE in oil reduces its irritation. As a result, under the action of DSPE-PEG-Tf, tumor CMP, oil, phospholipid, PEG derivative, and osmotic pressure modulator, the dual-targeting biomimetic liposome can significantly enhance the efficacy and prevent drug resistance while significantly reducing toxicity, thereby showing a desired cytotoxicity, cell arrest, or biological effect on relevant glioma cells.

The inventors have found that ELE and CTX encapsulated in a same nanoparticle at a mass ratio of 10:1 exhibit synergistic effects and reduce toxicity. A same effect can be achieved when the dosage of nanoparticles is only 25% of that of conventional CTX injection. Therefore, co-embedding ELE and CTX into nanoparticles is expected to achieve the best anti-glioma effect. The liposome is coupled to Tf, while CMP is embedded into the liposome to prepare a liposome containing ELE and CTX (Tf-ELE/CTX@BLIP), which is used for active targeted chemotherapy across the BBB and in situ glioma in mice. The inventors have studied the effects of Tf-ELE/CTX@BLIP on P-gp inhibition, active targeting, immune evasion, in vitro cytotoxicity, promotion of apoptosis, and in vivo distribution, and also have evaluated the antitumor activity and toxicity of Tf-ELE/CTX@BLIP against orthotopic glioma in mice.

Preferably, the oil is one or more selected from the group consisting of medium-chain triglyceride (MCT), soybean oil, palm oil, coconut oil, fish oil, hydrogenated oil, and animal oil.

Preferably, the phospholipid is one or more selected from the group consisting of soybean phospholipid, egg yolk phospholipid, hydrogenated phospholipid, and synthetic phospholipid.

Preferably, the PEG derivative is selected from the group consisting of D-α-tocopherol polyethylene glycol succinate (TPGS) and DSPE-PEG.

Preferably, the DSPE-PEG-Tf is selected from the group consisting of DSPE-PEG2000-Tf, DSPE-PEG3000-Tf, DSPE-PEG4000-Tf, and DSPE-PEG5000-Tf.

Preferably, the tumor CMP is one or more selected from the group consisting of RG2, C6, U251, U87, and BT-325.

The present disclosure further provides a preparation method of the dual-targeting biomimetic liposome with ELE and CTX, including the following steps:

(1) preparing an oil phase: mixing the oil, the phospholipid, the cholesterol, the PEG derivative, the ELE, the DSPE-PEG-Tf, and the CTX according to a specified ratio to allow melting at 70° C. to 100° C. to obtain the oil phase;

(2) preparing an aqueous phase: dissolving the osmotic pressure regulator in the water under thermal insulation at 50° C. to 70° C. to obtain the aqueous phase; and (3) conducting mixing and extrusion: adding the oil phase into the aqueous phase to allow high-speed shearing and ultrasonic disruption in sequence, adding the tumor CMP, and extruding a resulting mixture repeatedly through extrusion to pass through a filter membrane to obtain the dual-targeting biomimetic liposome with ELE and CTX.

Preferably, the osmotic pressure regulator in step (2) is one or more selected from the group consisting of the glycerol, the glucose, the sucrose, the trehalose, the maltose, and the mannitol.

Preferably, the high-speed shearing is conducted at 8,000 r/min to 15,000 r/min for 20 min to 40 min and the ultrasonic disruption is conducted at 230 W to 240 W in step (3).

Preferably, the filter membrane in step (3) includes a 0.45 μm filter membrane and a 0.22 μm filter membrane.

The present disclosure further provides use of the dual-targeting biomimetic liposome with ELE and CTX in treatment of brain glioma and other types of glioma.

Therefore, the present disclosure has the following beneficial effects:

(1) In the present disclosure, ELE, CTX, DSPE-PEG-Tf, tumor CMP, and PEG derivative are simultaneously encapsulated in a liposome, such that the ELE and CTX act synergistically on glioma cells, thereby improving the BBB permeability of the drug and the uptake rate of glioma cells, and then significantly enhancing the targeting efficiency and efficacy. Meanwhile, the present disclosure significantly reduces the toxic and side effects of CTX and the irritation of ELE, significantly improves safety, and effectively avoids the side effects of the drug on normal brain cells and other tissues and organs. The dual-targeting biomimetic liposome is mainly used for the treatment of RG2 syngeneic glioma and other types of glioma. Compared with the existing technology, the dual-targeting biomimetic liposome with ELE and CTX significantly improves the efficacy of anti-drug-resistant tumors and significantly improves safety.

(2) In the present disclosure, the dual-targeting biomimetic liposome shows moderate particle size, uniform particle size distribution, and desirable stability, and is extremely convenient for clinical use.

(3) In the present disclosure, the preparation method has simple processes and strong repeatability, and is suitable for large-scale production.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 6A:
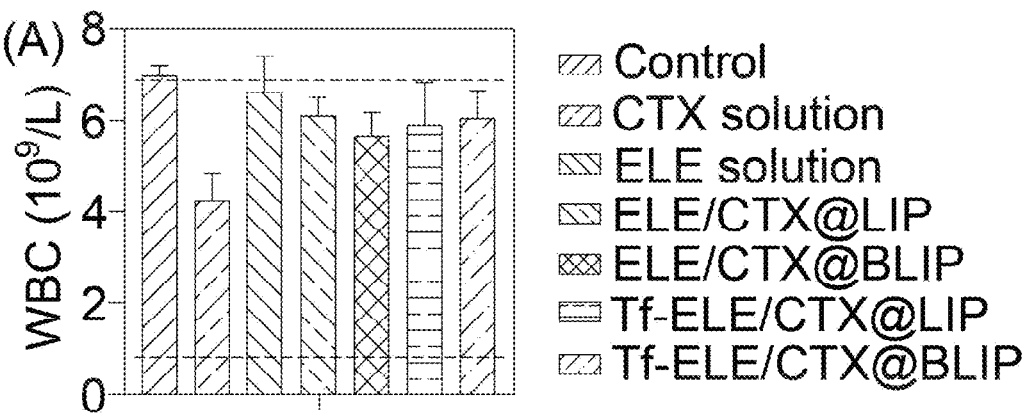
Figure 6B:
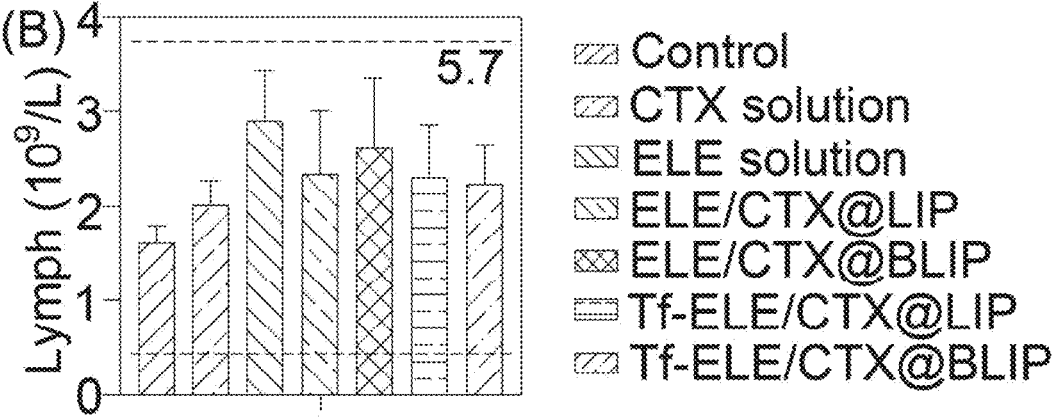
Figure 6C:
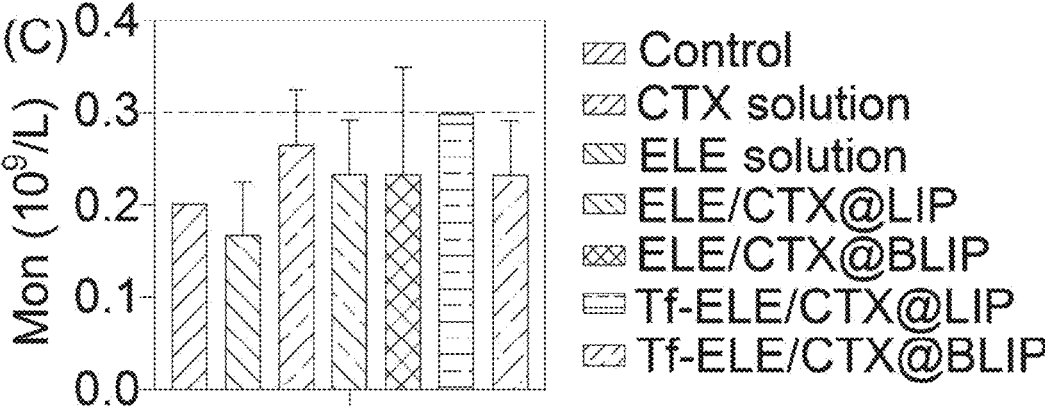
Figure 6D:
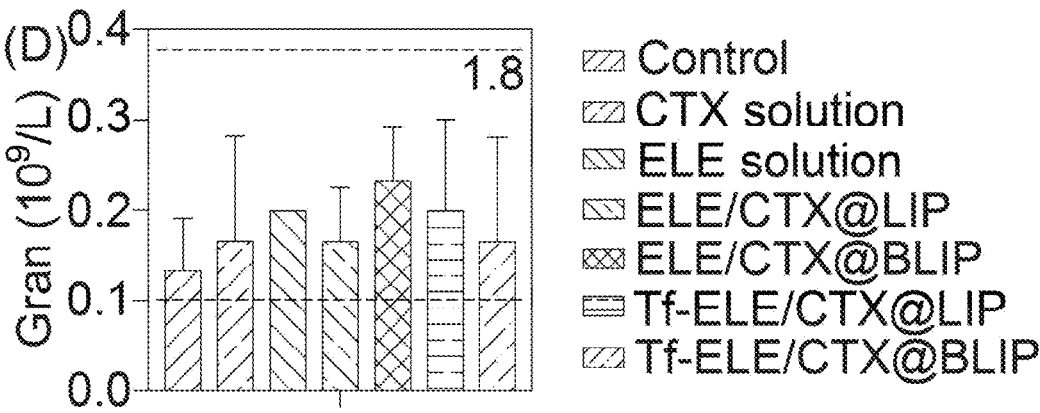
Figure 6E:
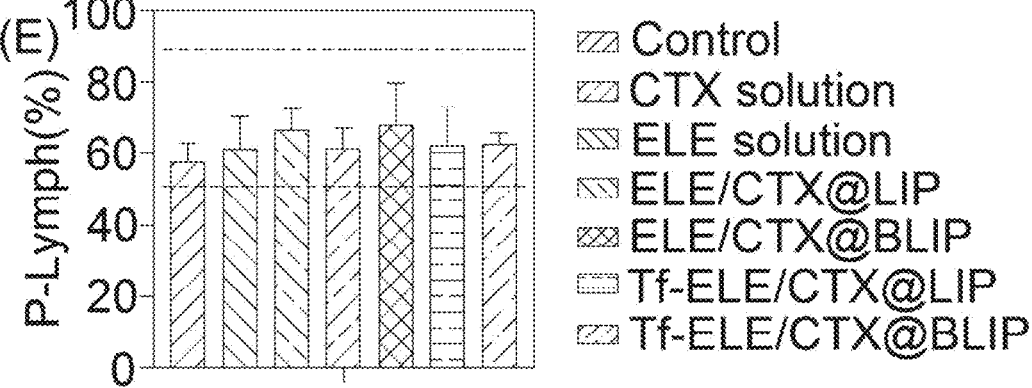
Figure 6F:
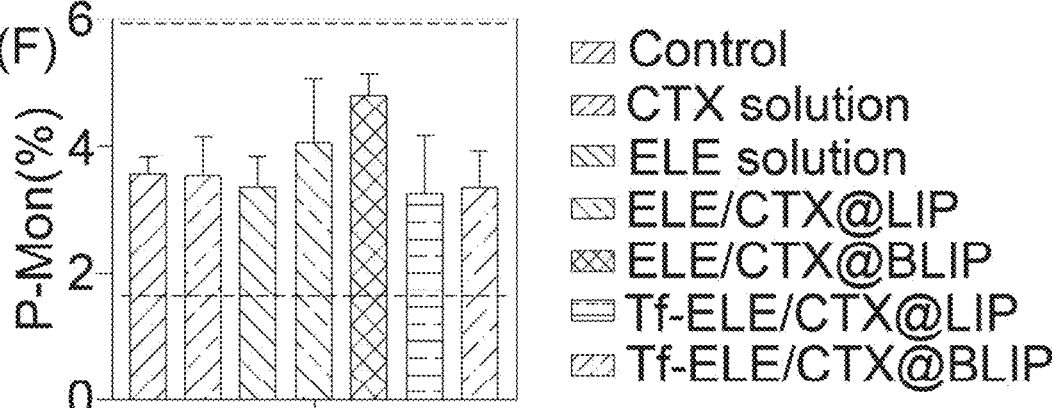
Figure 6G:
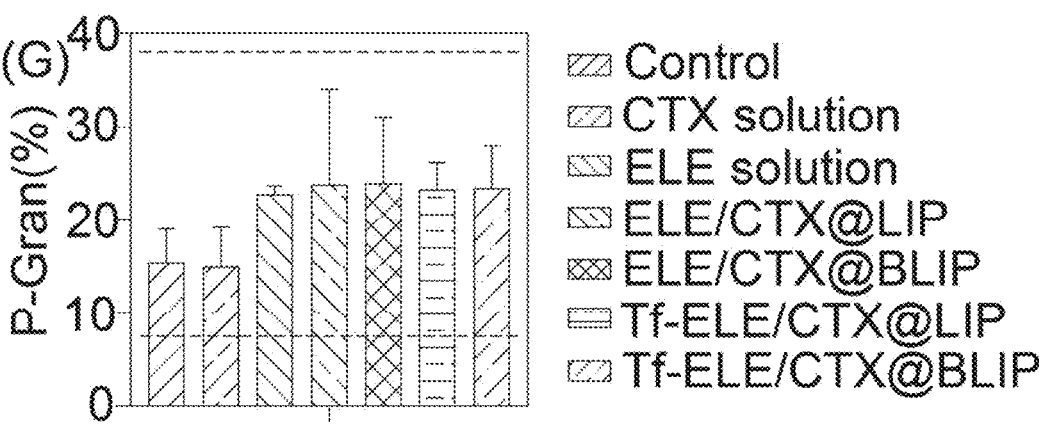
Figure 6H:
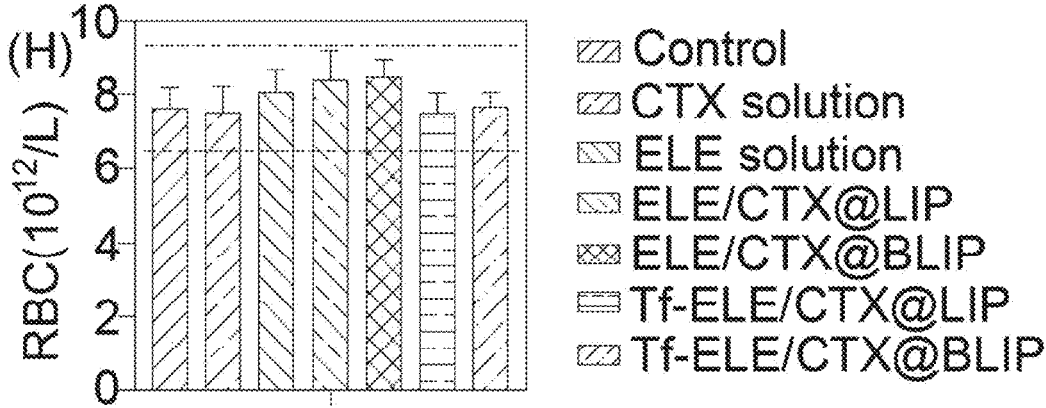
Figure 6I:
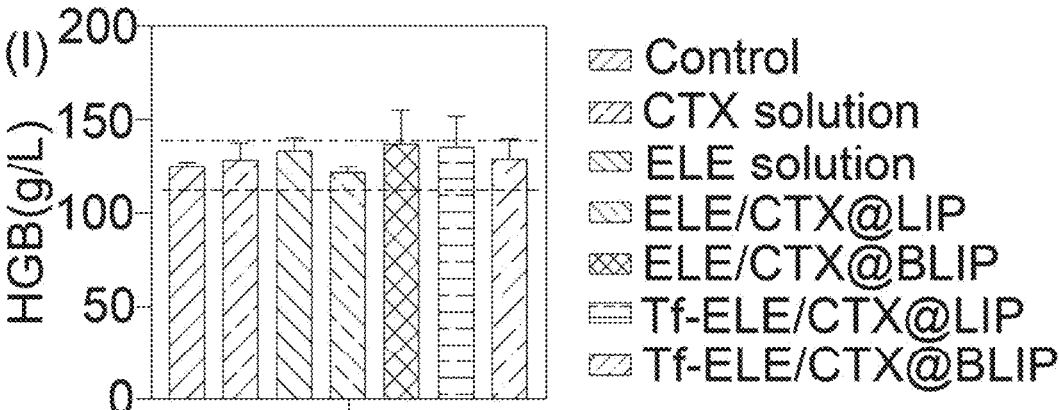
Figure 6J:
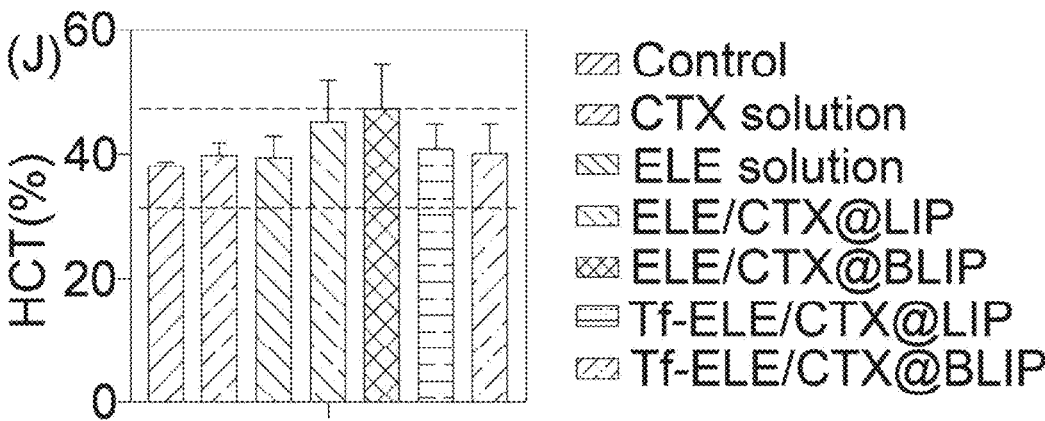
Figure 6K:
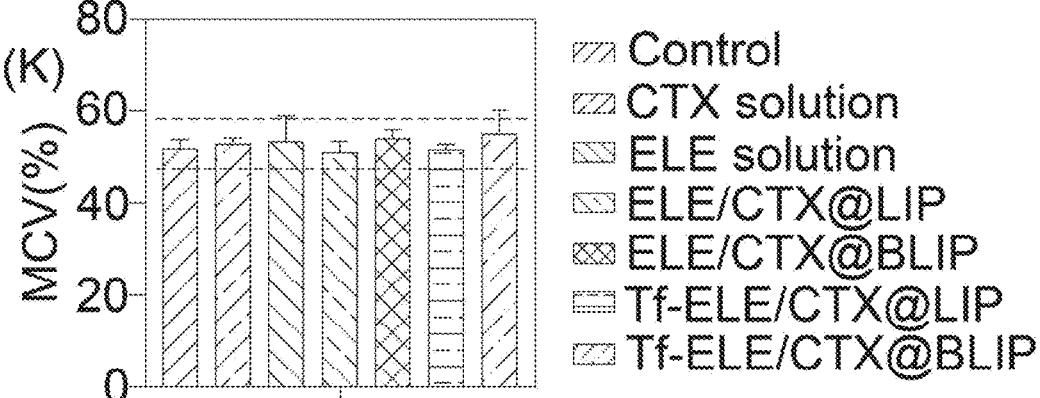
Figure 6L:
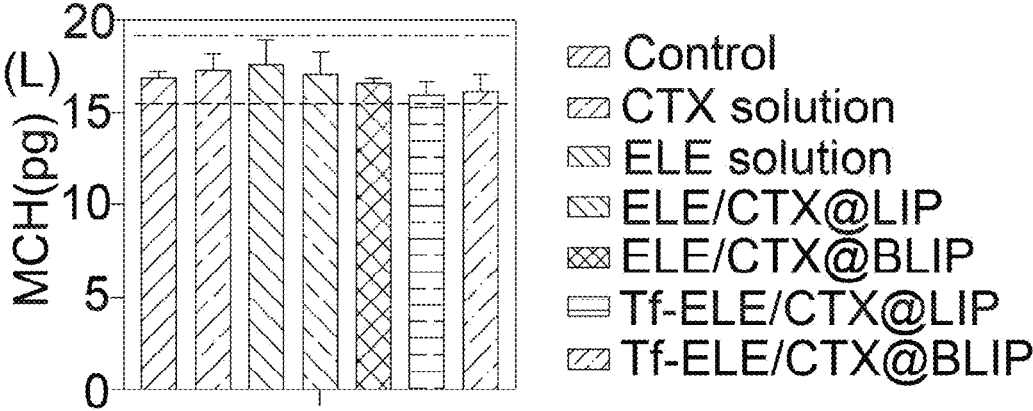
Figure 6M:
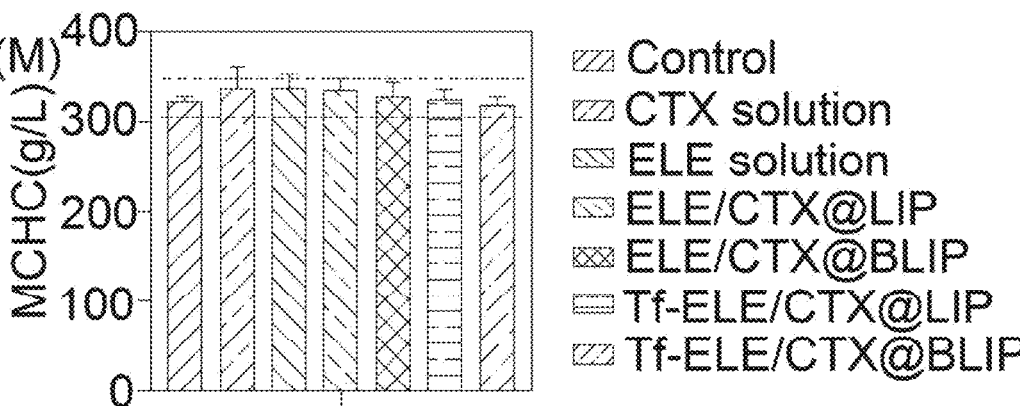
Figure 6N:
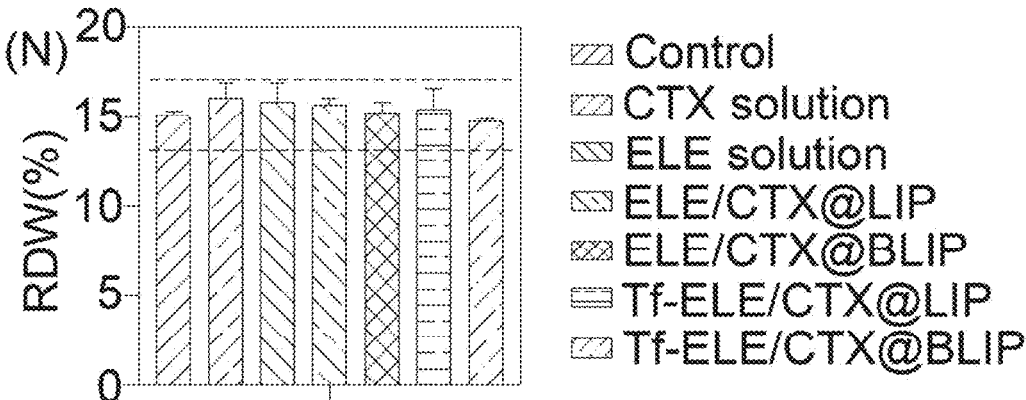
Figure 6O:
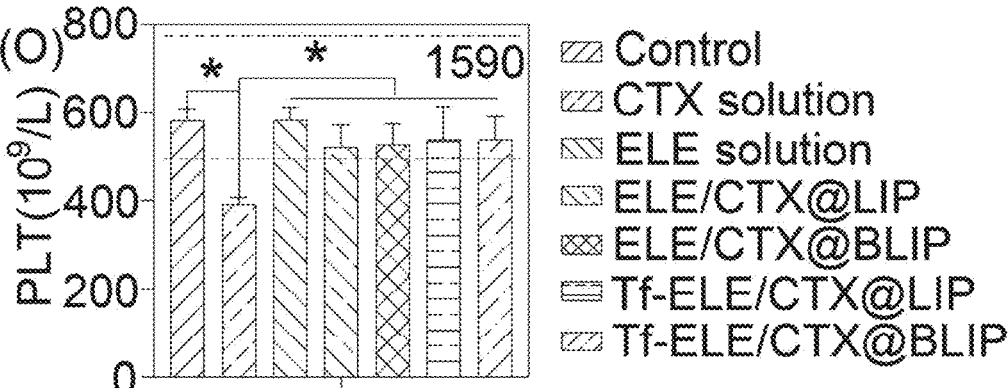
Figure 6P:
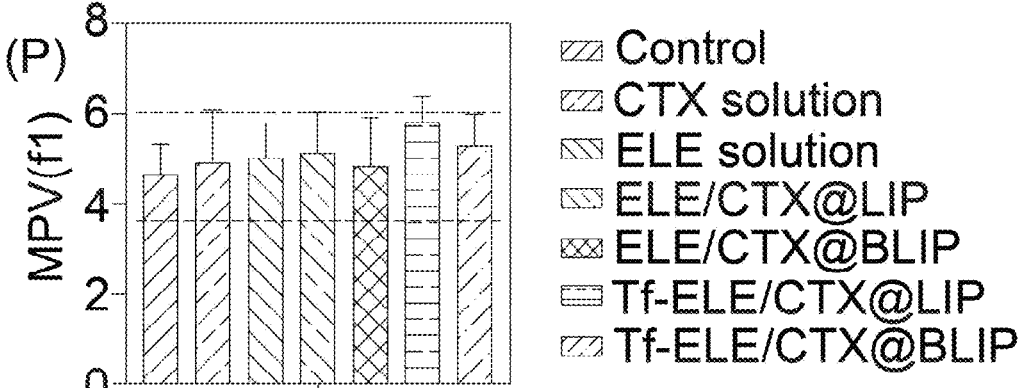
Figure 6Q:
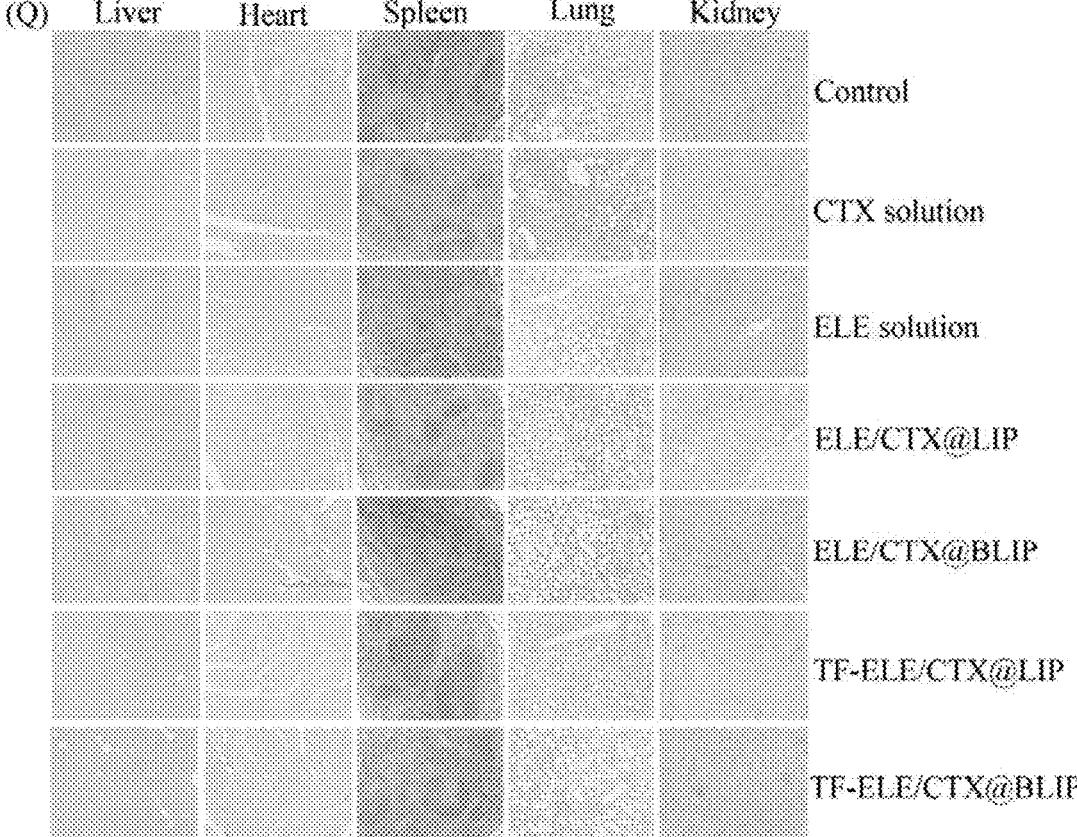
Figure 7A:
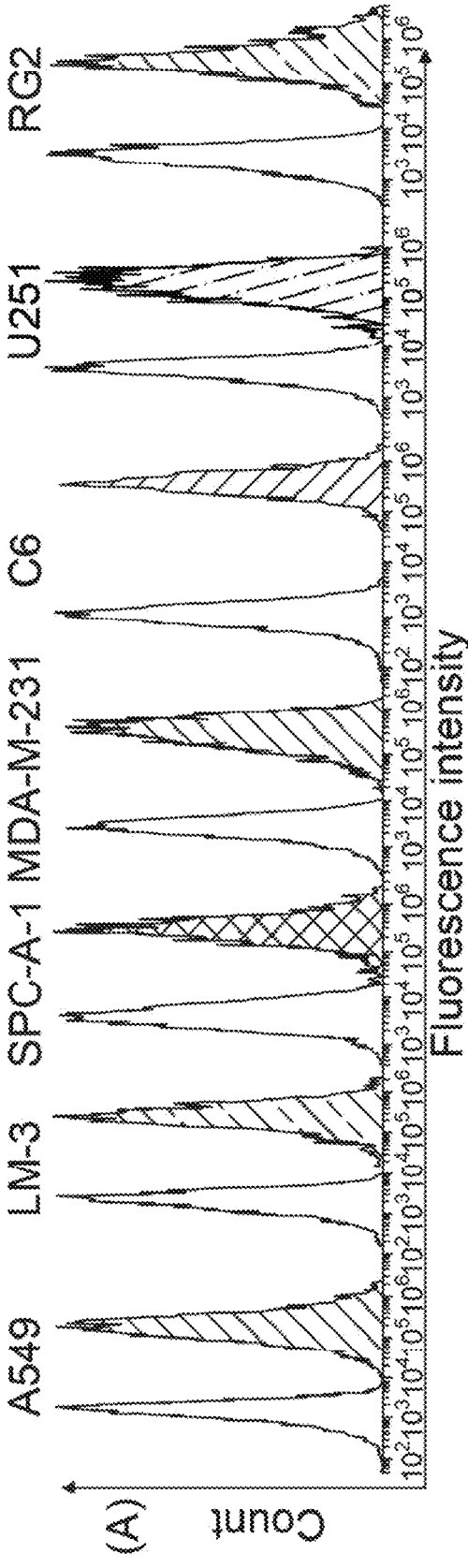
Figure 7B:
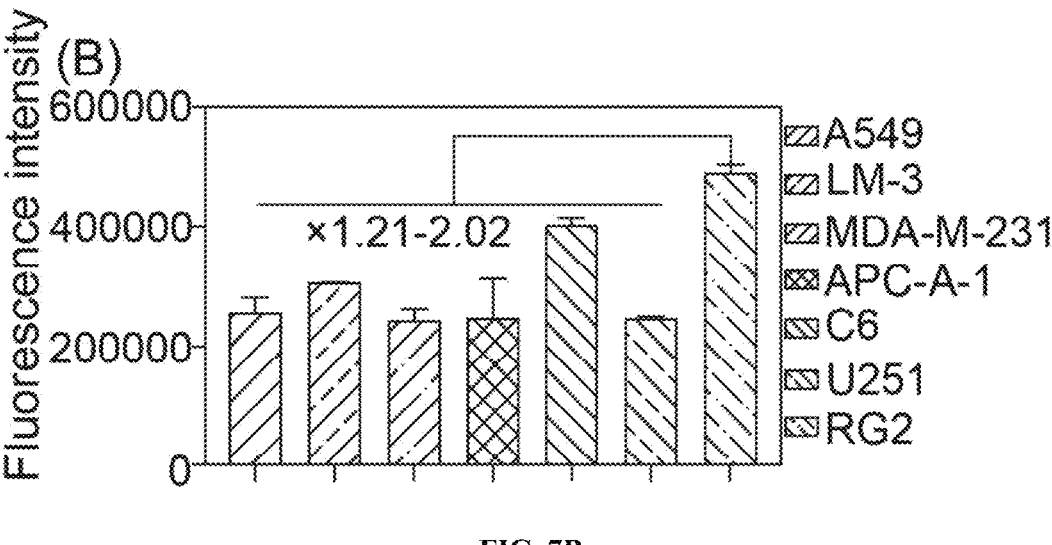
Figure 7C:
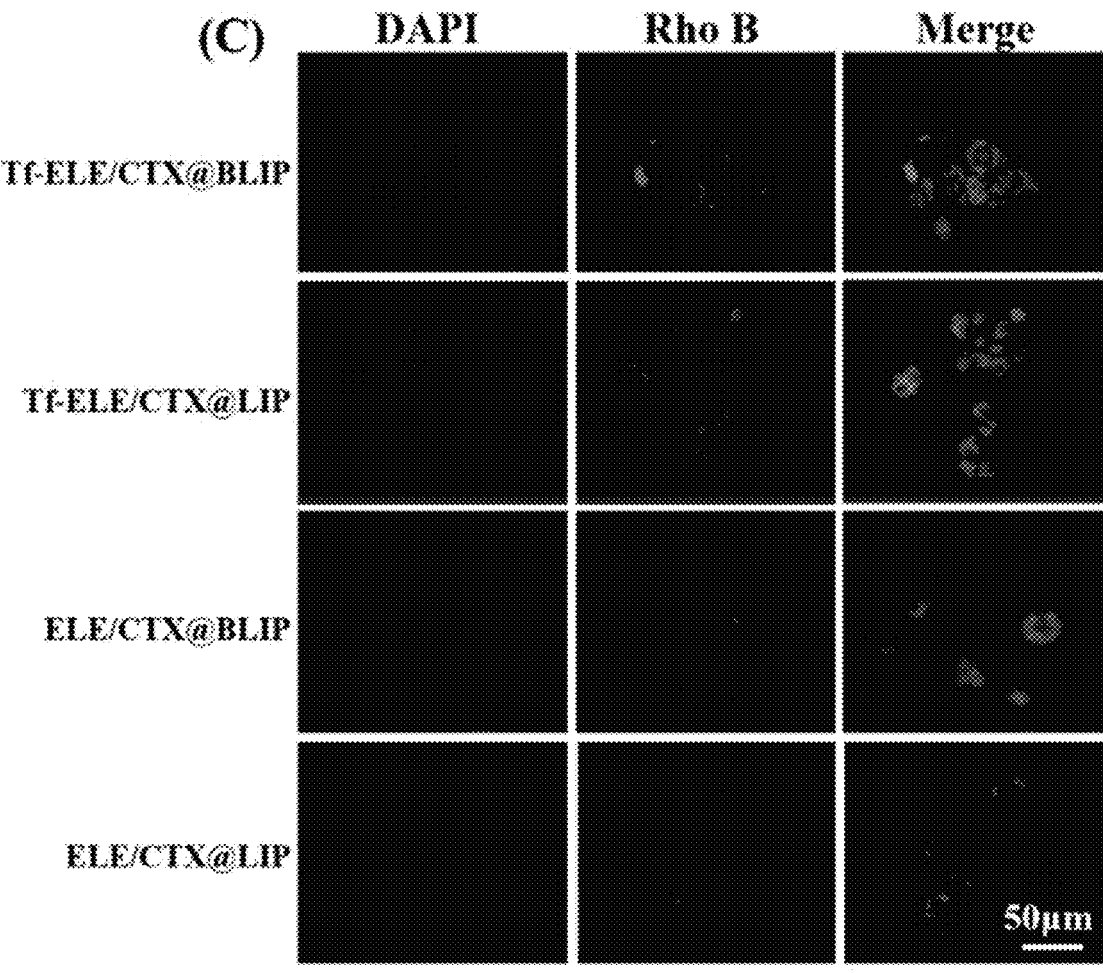
Figure 7D:
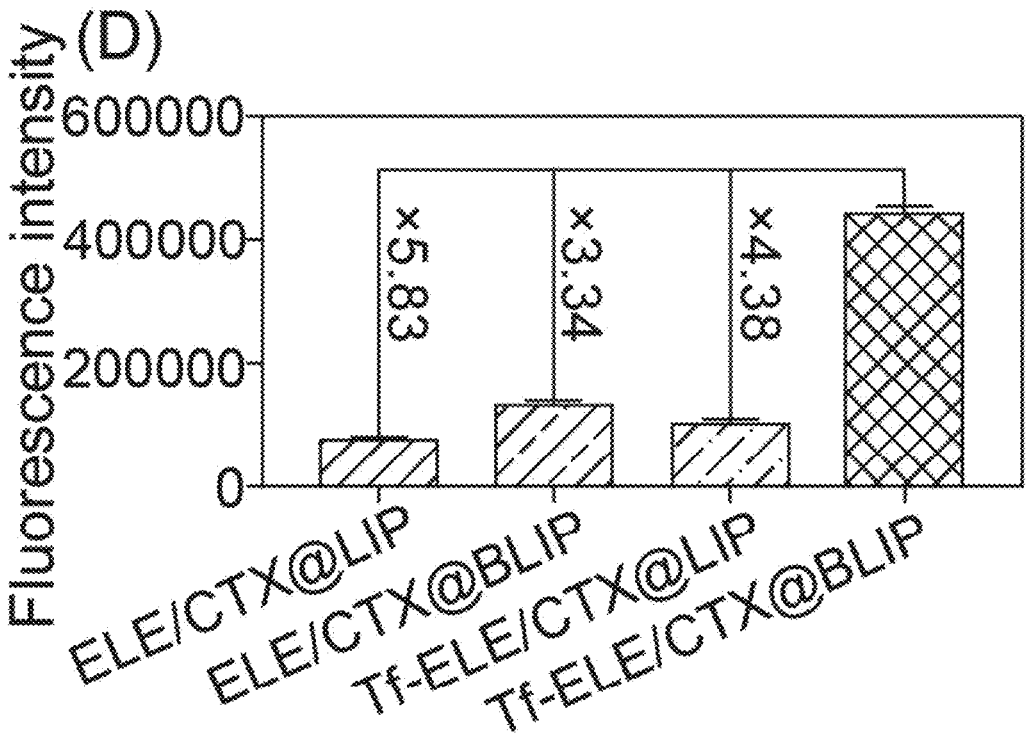
Figure 7E:
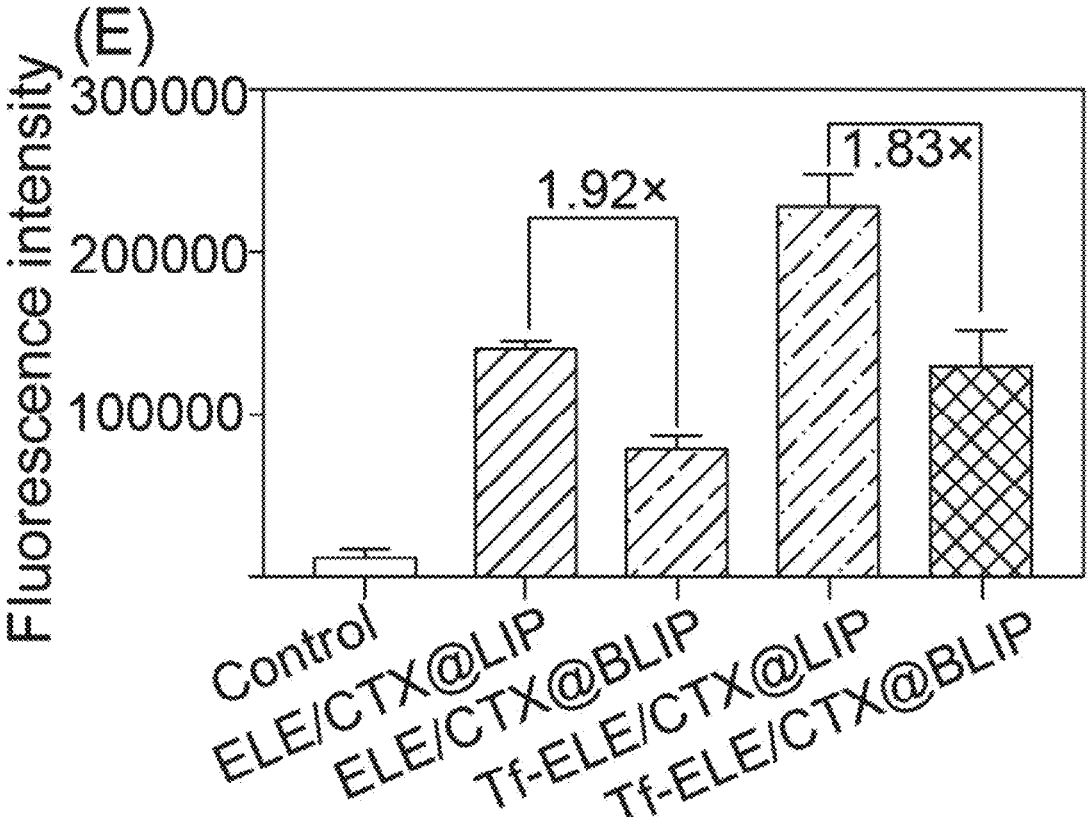
Figure 7F:
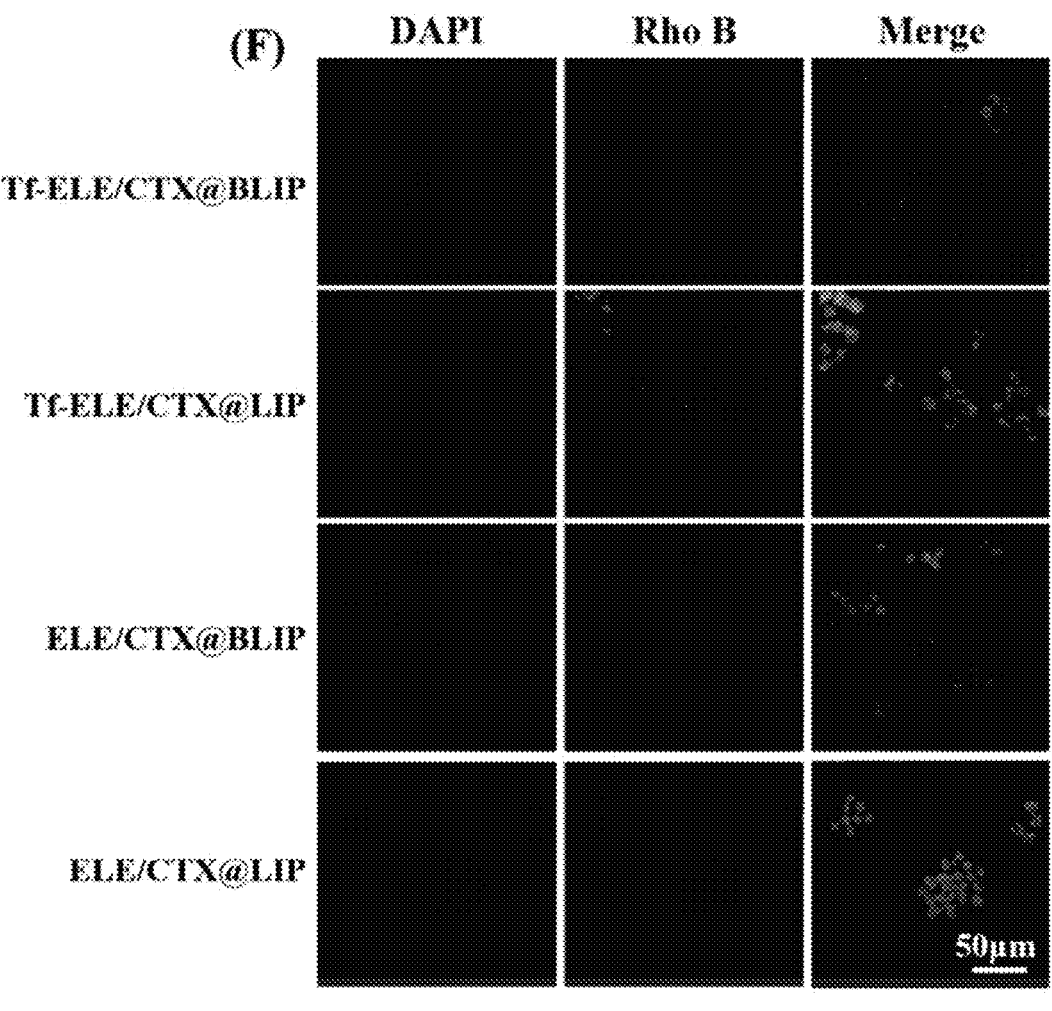
Figure 8A:
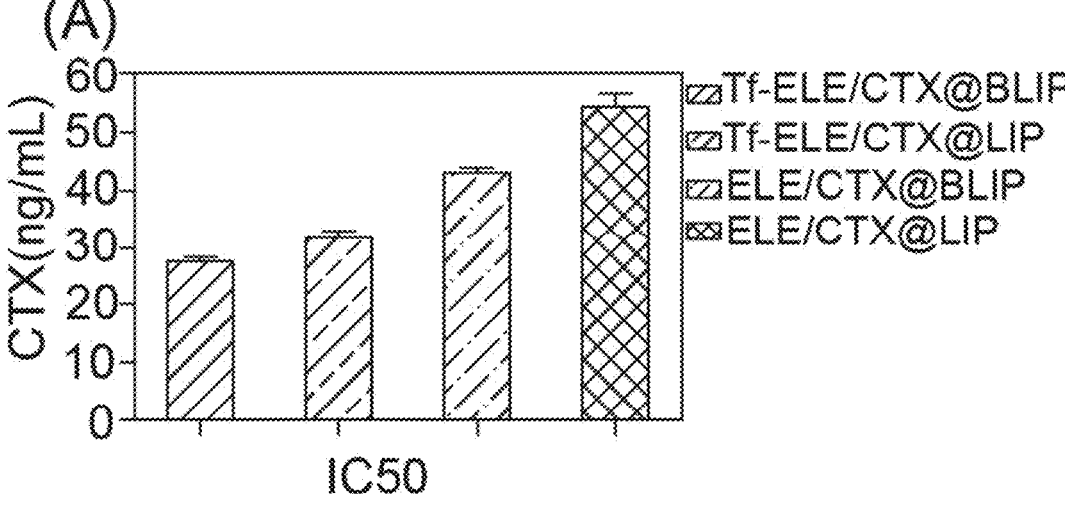
Figure 8B:
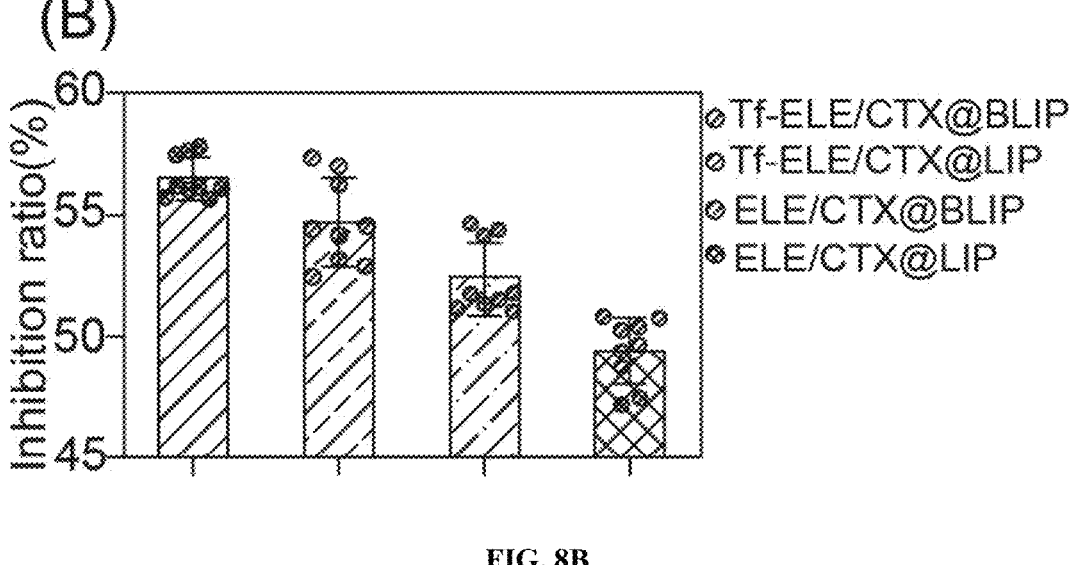
Figure 8C:
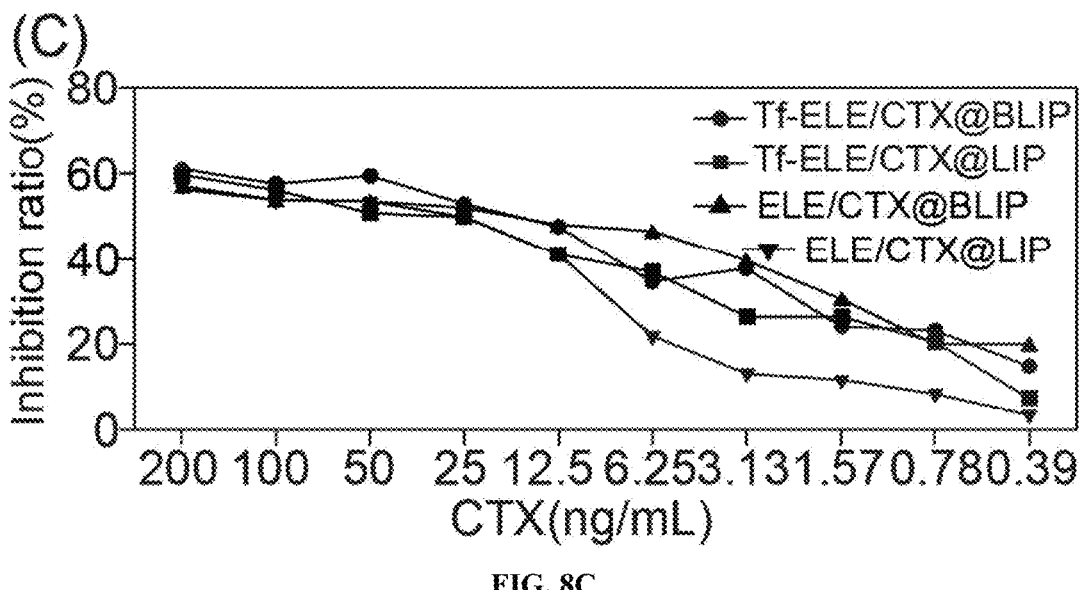
Figure 8D:
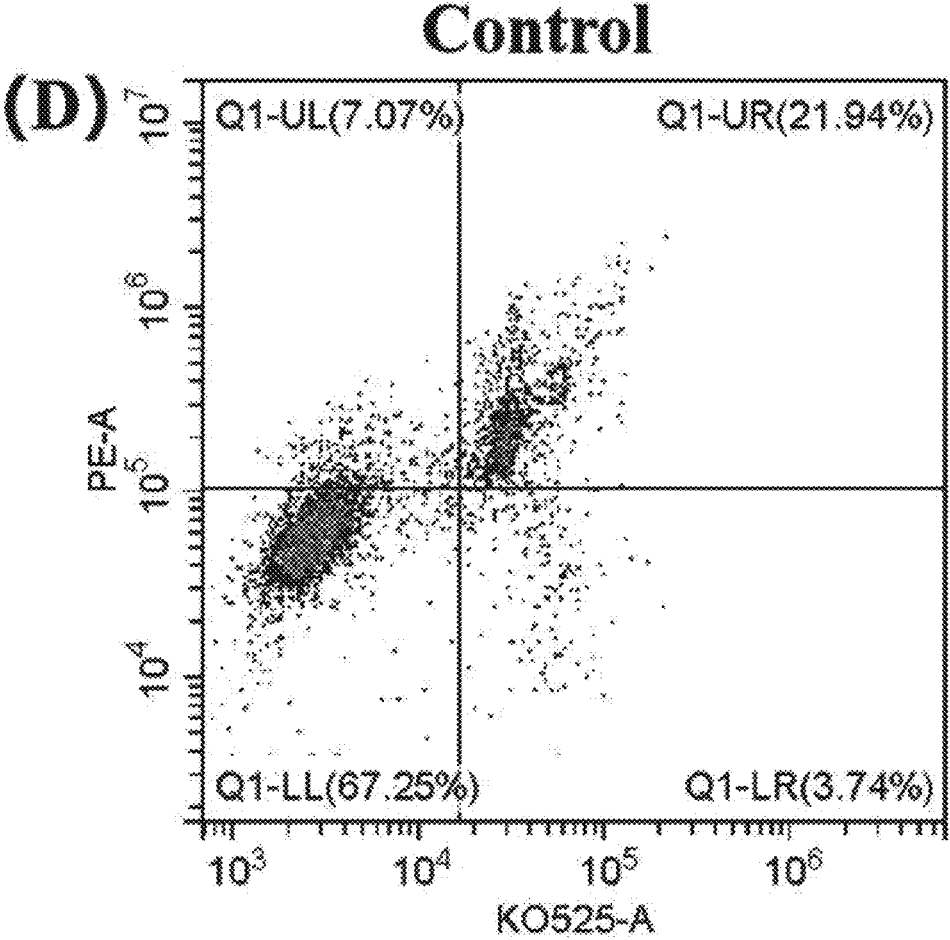
Figure 8E:
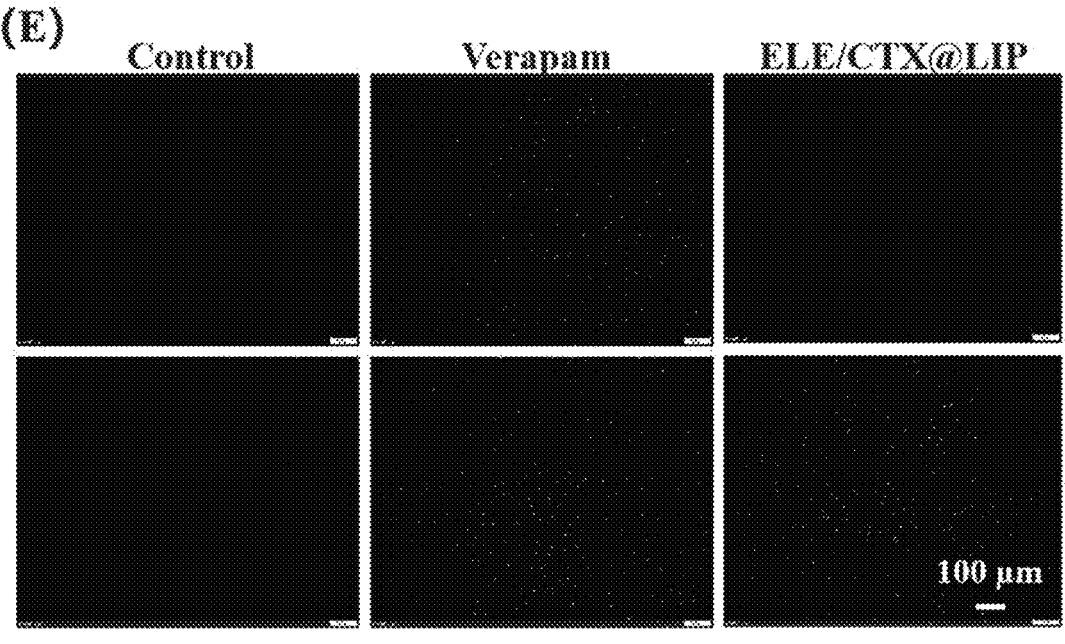
Figure 8F:
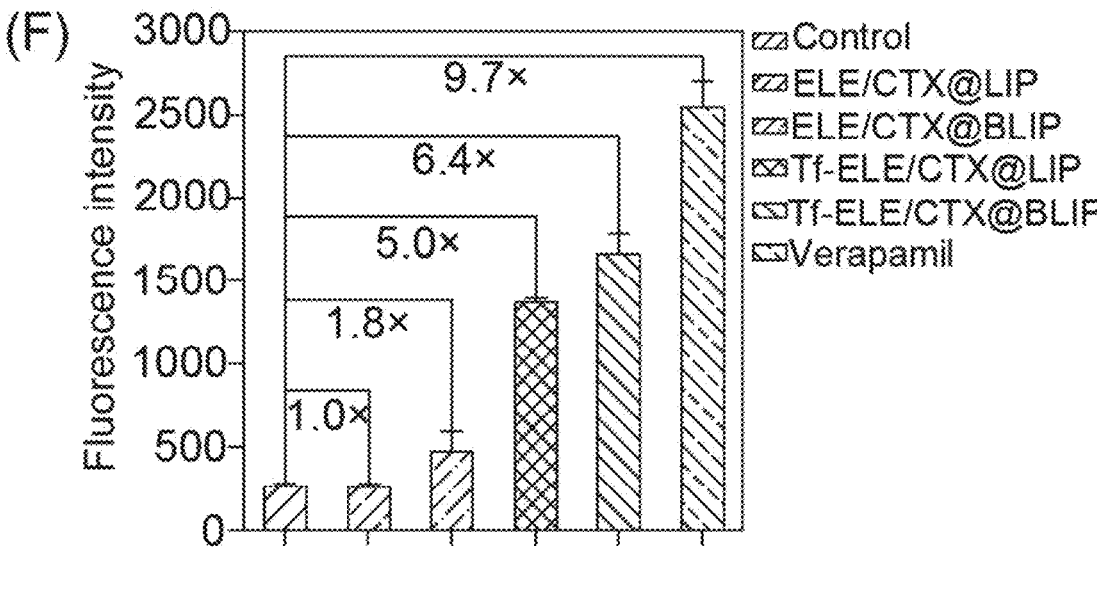
Figure 8G:
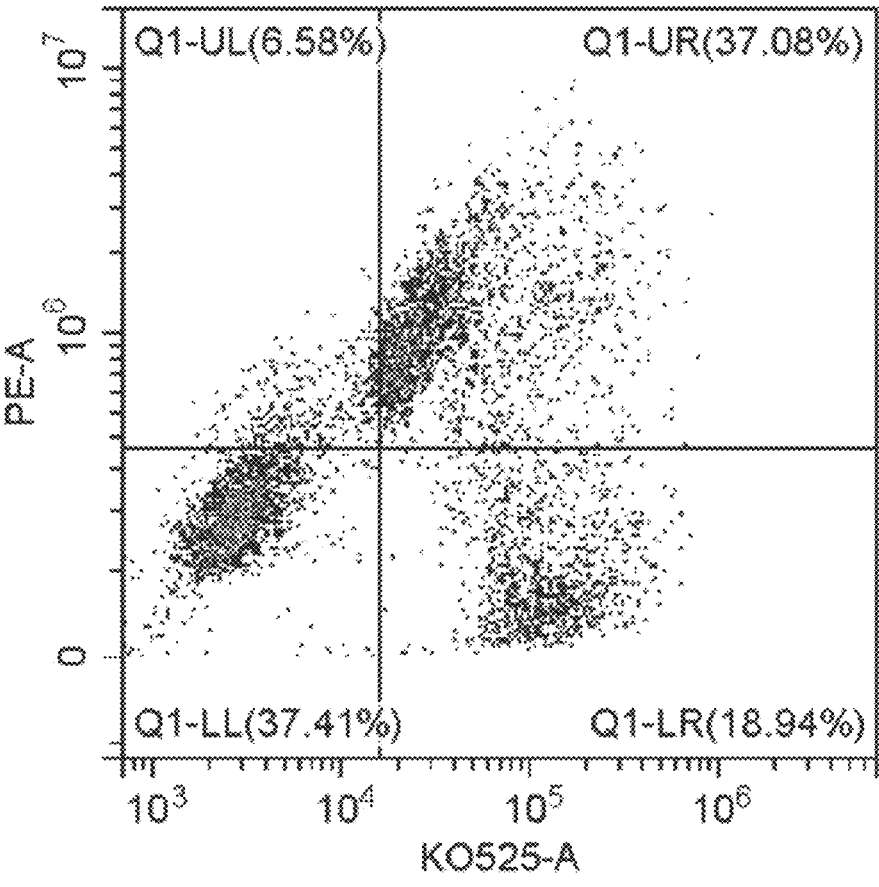
Figure 8H:
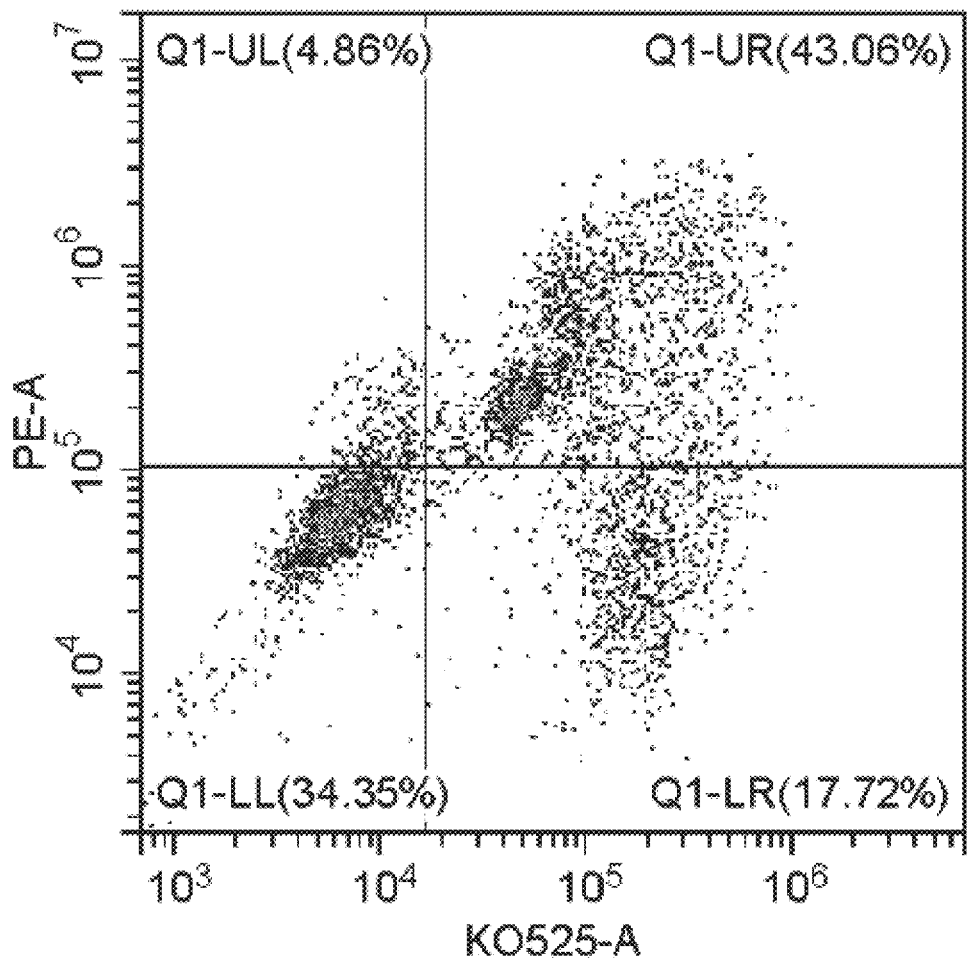
Figure 8I:
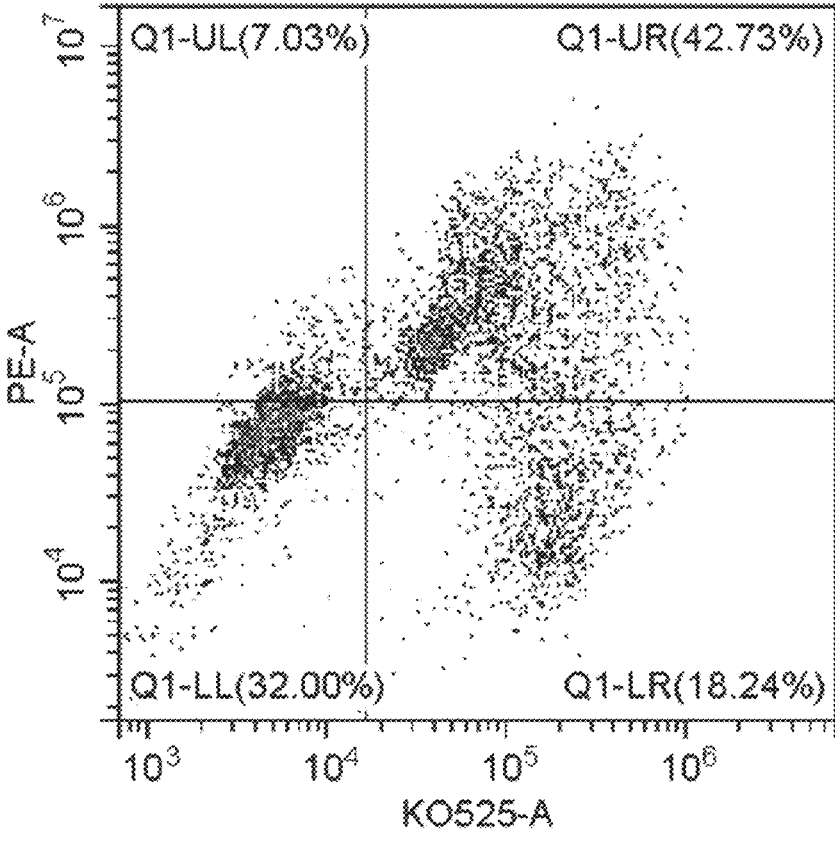
Figure 8J:
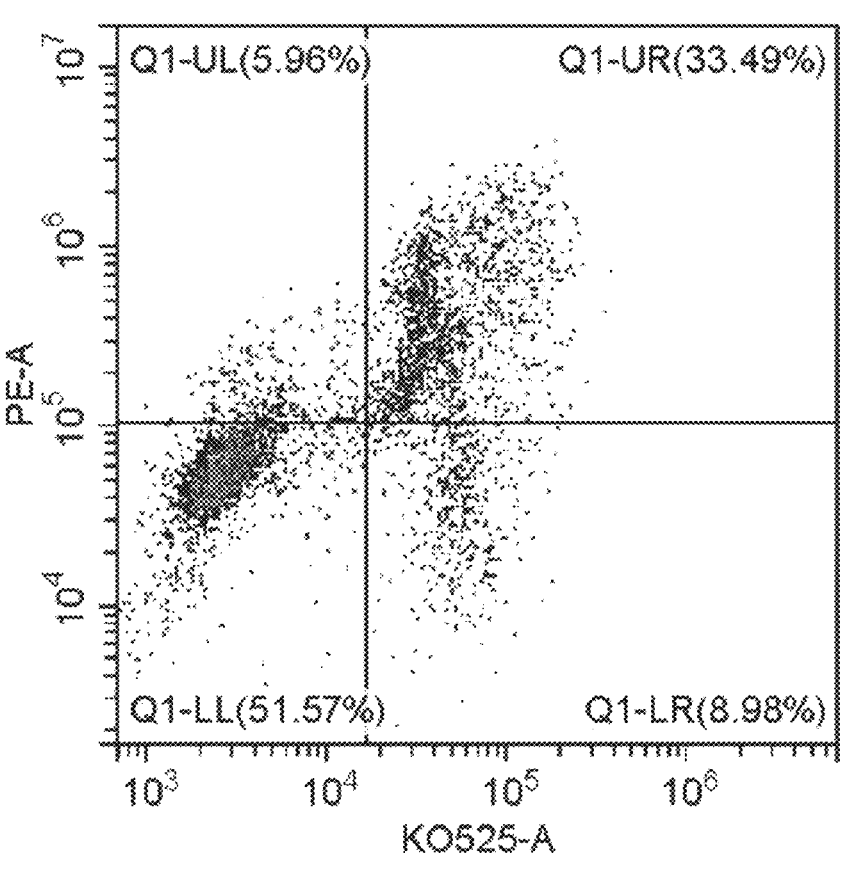
Figure 8K:
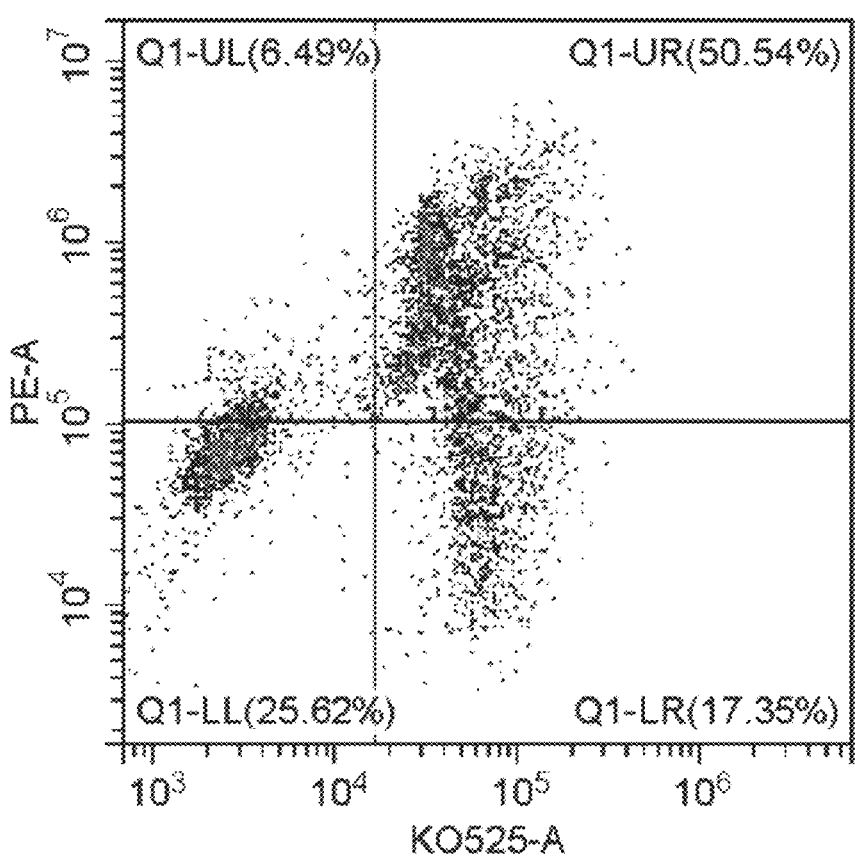

FIGS. 4A-D show the tumor fluorescence intensity, survival period, and body weight changes after treatment of dual-targeting biomimetic liposome with ELE and CTX prepared in Example 1 of the present disclosure and the control preparation;

FIGS. 5A-D show the effects of dual-targeting biomimetic liposome with ELE and CTX prepared in Example 1 of the present disclosure and the control preparation after treatment;

FIGS. 6A-Q show the safety comparison between the dual-targeting biomimetic liposome with ELE and CTX prepared in Example 1 of the present disclosure and the control preparation; where treatments in FIG. 3 to FIGS. 6A-Q are as follows: Control group, physiological saline; ELE solution group, ELE injection, 25 mg/kg, once every other day; CTX solution group, CTX injection; ELE/CTX-LIP group, ELE/CTX liposome; ELE/CTX-BLIP group, ELE/CTX biomimetic liposome; Tf-ELE/CTX-LIP group, Tf-modified ELE/CTX targeting liposome; Tf-ELE/CTX-BLIP group, dual-targeting biomimetic liposome with ELE and CTX; and the CTX solution group, ELE/CTX-LIP group, ELE/CTX-BLIP group, Tf-ELE/CTX-LIP group, and Tf-ELE/CTX-BLIP groups are administered at 2.5 mg/kg (calculated as CTX) for the first time, and then 0.625 mg/kg/time, once every other day;

FIGS. 7A-F show the homologous targeting and immune evasion of dual-targeting biomimetic liposome with ELE and CTX prepared in Example 1 of the present disclosure; where (A) flow cytometry analysis and (B) average fluorescence intensity of Rho B after Tf-ELE/CTX@BLIP acted on A549, LM-3, SPC-A-1, MDA-M-231, U251, C6, and RG2 for 2 h; (C) laser confocal imaging and (D) flow cytometry analysis of the average fluorescence intensity of Rho B in RG2 glioma cells treated with Tf-ELE/CTX@BLIP, Tf-ELE/CTX@LIP, ELE/CTX@BLIP, and ELE/CTX@LIP for 2 h; (E) flow cytometry analysis and (F) laser confocal imaging of RAW264.7 cells after treated with Tf-ELE/CTX@BLIP, Tf-ELE/CTX@LIP, ELE/CTX@BLIP, and ELE/CTX@LIP for 2 h; and FIGS. 8A-F show the cytotoxicity, pro-apoptosis, and P-gp inhibitory effect of dual-targeting biomimetic liposome with ELE and CTX prepared in Example 1 of the present disclosure; where (A) IC50, (B) cell inhibition rate (C CTX=50 ng/ml), (C) cell inhibition rate (C CTX 0.4 ng/mL to 200 ng/mL); (D) apoptosis of untreated RG2 cells incubated with Tf-ELE/CTX@BLIP, Tf-ELE/CTX@LI, ELE/CTX@BLIP, and ELE/CTX@LIP for 48 h; (E) confocal image of Rho 123 uptake, (F) quantitative analysis of Rho 123 uptake in bEnd.3 cells incubated with Tf-ELE/CTX@BLIP, Tf-ELE/CTX@LI, ELE/CTX@BLIP, and ELE/CTX@LIP for 2 h;

FIG. 8G is apoptosis of RG2 cells after incubation with ELE/CTX@BLIP for 48 h;

FIG. 8H is apoptosis of RG2 cells incubated with Tf-ELE/CTX@LIP for 48 h;

FIG. 8I is apoptosis of RG2 cells after incubation with Tf-ELE/CTX@BLIP for 48 h;

FIG. 8J is apoptosis of RG2 cells after incubation with CTX for 48 h;

FIG. 8K is apoptosis of RG2 cells incubated with ELE/CTX for 48 h; and

Figure 8L:
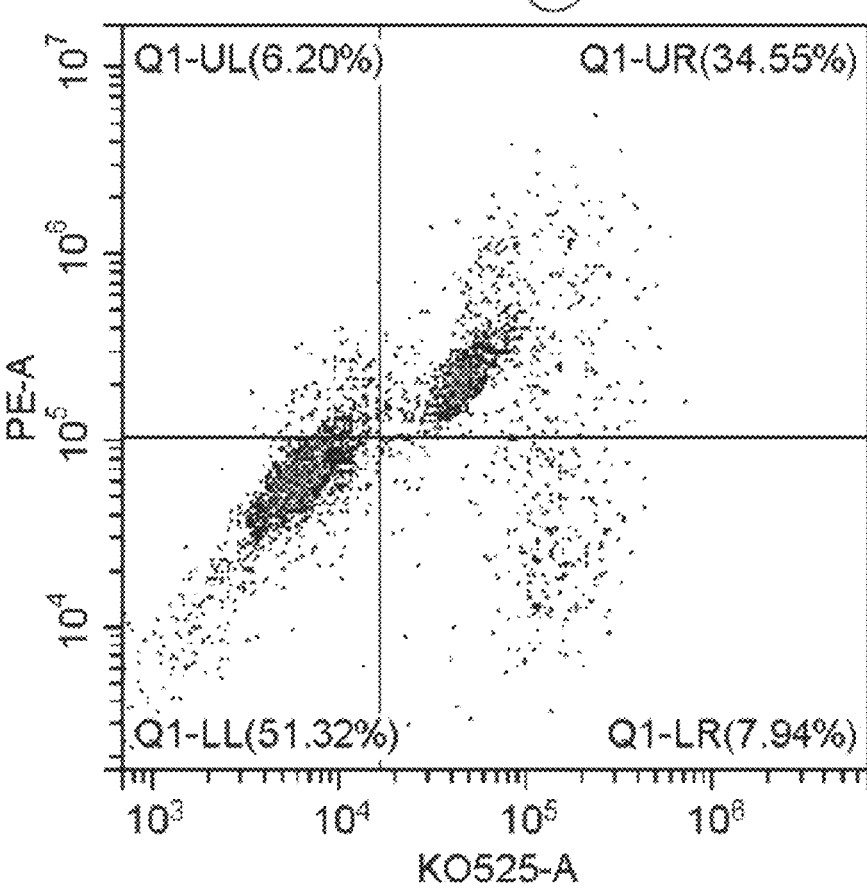

FIG. 8L is apoptosis of RG2 cells incubated with ELE/CTX@LIP for 48 h.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components, or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The technical solutions of the present disclosure are further described below with reference to specific examples.

In the present disclosure, all raw materials and equipment used are commercially available or are commonly used in the art. Unless otherwise specified, the methods in the examples are all conventional methods in the art.

Example 1

(ELE 0.4%, absolute ethanol 1.25%, CTX 0.04%, oil 0.5%, PEG derivative 0.5%, phospholipid 2.5%, cholesterol 0.1%, DSPE-PEG2000-Tf 0.05%, tumor CMP 0.025%).

A dual-targeting biomimetic liposome with ELE and CTX was provided, where each 20 mL of the dual-targeting biomimetic liposome with ELE and CTX included 8 mg of the CTX, 0.25 mL of the absolute ethanol, 100 mg of the MCT, 100 mg of the TPGS, 500 mg of the soybean phospholipid, 80 mg of the ELE, 10 mg of the DSPE-PEG2000-Tf, 20 mg of the cholesterol, 5 mg of the tumor CMP, 520 mg of the glycerol, and the water as a balance.

A preparation method of the dual-targeting biomimetic liposome with ELE and CTX included the following steps:
  (1) preparation of an oil phase: the CTX was dissolved in the absolute ethanol under ultrasonic treatment, a resulting solution was added with the MCT, TPGS, soybean phospholipid, ELE, cholesterol, and DSPE-PEG2000-Tf, and then dissolved in a water bath at 80° C.;
  (2) preparation of an aqueous phase: the glycerol was dissolved in water in a 60° C. water bath; and
  (3) mixing and extrusion: the oil phase was added into the aqueous phase, sheared in a 60° C. water bath at 10,000 r/min for 30 min, and then subjected to ultrasonic disruption with a probe; 5 mg of the tumor CMP was added, and an obtained mixture was repeatedly extruded through 0.45 μm and 0.22 μm filter membranes in sequence by an extrusion method to obtain the dual-targeting biomimetic liposome with ELE and CTX.

Example 2 (ELE 0.15%)

This example differed from Example 1 in that 30 mg of the ELE was used.

Example 3 (ELE 0.75%)

This example differed from Example 1 in that 150 mg of the ELE was used.

Example 4 (CTX 0.015%)

This example differed from Example 1 in that 3 mg of the CTX was used.

Example 5 (CTX 0.07%)

This example differed from Example 1 in that 14 mg of the CTX was used.

Example 6 (Absolute Ethanol 0.5%)

This example differed from Example 1 in that 0.1 mL of the absolute ethanol was used.

Example 7 (Absolute Ethanol 2.5%)

This example differed from Example 1 in that 0.5 mL of the absolute ethanol was used.

Example 8 (MCT 0.25%)

This example differed from Example 1 in that 50 mg of the MCT was used.

Example 9 (MCT 1%)

This example differed from Example 1 in that 200 mg of the MCT was used.

Example 10 (TPGS 0.25%)

This example differed from Example 1 in that 50 mg of the TPGS was used.

Example 11 (TPGS 1%)

This example differed from Example 1 in that 200 mg of the TPGS was used.

Example 12 (Soybean Phospholipid 1%)

This example differed from Example 1 in that 200 mg of the soybean phospholipid was used.

Example 13 (Soybean Phospholipid 5%)

This example differed from Example 1 in that 1,000 mg of the soybean phospholipid was used.

Example 14 (Cholesterol 0.05%)

This example differed from Example 1 in that 10 mg of the cholesterol was used.

Example 15 (Cholesterol 0.2%)

This example differed from Example 1 in that 40 mg of the cholesterol was used.

Example 16 (DSPE-PEG2000-Tf 0.025%)

This example differed from Example 1 in that 5 mg of the DSPE-PEG2000-Tf was used.

Example 17 (DSPE-PEG2000-Tf 0.1%)

This example differed from Example 1 in that 20 mg of the DSPE-PEG2000-Tf was used.

Example 18 (Tumor CMP 0.0125%)

This example differed from Example 1 in that 2.5 mg of the tumor CMP RG2 was used.

Example 19 (Tumor CMP 0.005%)

This example differed from Example 1 in that 1 mg of the tumor CMP RG2 was used.

Example 20

A dual-targeting biomimetic liposome with ELE and CTX was provided, where each 20 mL of the dual-targeting biomimetic liposome with ELE and CTX included 8 mg of the CTX, 0.25 mL of the absolute ethanol, 50 mg each of palm oil and coconut oil, 100 mg of the DSPE-PEG, 500 mg of the DSPC synthetic phospholipid, 80 mg of the ELE, 10 mg of the DSPE-PEG5000-Tf, 20 mg of the cholesterol, 5 mg of the tumor CMP C6, 260 mg each of glucose and sucrose, and the water as a balance.

A preparation method of the dual-targeting biomimetic liposome with ELE and CTX included the following steps:

(1) preparation of an oil phase: the CTX was dissolved in the absolute ethanol under ultrasonic treatment, a resulting solution was added with the palm oil, coconut oil, DSPE-PEG, synthetic phospholipids, ELE, cholesterol, DSPE-PEG5000-Tf, and then dissolved in a water bath at 80° C.;

(2) preparation of an aqueous phase: the glucose and sucrose were dissolved in water in a 60° C. water bath; and (3) mixing and extrusion: the oil phase was added into the aqueous phase, sheared in a 60° C. water bath at 10,000 r/min for 30 min, and then subjected to ultrasonic disruption with a probe; 5 mg of the tumor CMP C6 was added, and an obtained mixture was repeatedly extruded through 0.45 μm and 0.22 μm filter membranes in sequence by an extrusion method to obtain the dual-targeting biomimetic liposome with ELE and CTX.

Result Testing:

I. The particle size and potential of the dual-targeting biomimetic liposome with ELE and CTX prepared in each example was separately detected using a nanoparticle size potentiometer, and the results were shown in Table 1.

US 12,691,066 B2

11

TABLE 1

Particle size, distribution, and potential of 3 batches
of dual-targeting biomimetic liposome with ELE and CTX

| Item | Average intensity particle size (nm) | Average PI |
|---|---|---|
| Example 1 | 135.1 ± 4.2 | 0.263 ± 0.018 |
| Example 2 | 132.9 ± 0.9 | 0.204 ± 0.010 |
| Example 3 | 118.2 ± 0.5 | 0.207 ± 0.006 |
| Example 4 | 123.2 ± 1.6 | 0.202 ± 0.019 |
| Example 5 | 153.8 ± 3.1 | 0.216 ± 0.020 |
| Example 6 | 133.2 ± 3.5 | 0.227 ± 0.015 |
| Example 7 | 121.6 ± 1.7 | 0.205 ± 0.01 |
| Example 8 | 137.6 ± 0.9 | 0.216 ± 0.013 |
| Example 9 | 134.9 ± 3.0 | 0.190 ± .024 |
| Example 10 | 137.8 ± 2.3 | 0.209 ± 0.006 |
| Example 11 | 134.6 ± 2.9 | 0.222 ± 0.016 |
| Example 12 | 118.1 ± 2.7 | 0.208 ± 0.013 |
| Example 13 | 130.0 ± 2.6 | 0.271 ± 0.006 |
| Example 14 | 145.0 ± 2.0 | 0.293 ± 0.012 |
| Example 15 | 107.1 ± 0.7 | 0.234 ± 0.048 |
| Example 16 | 138.6 ± 2.1 | 0.280 ± 0.016 |
| Example 17 | 116.4 ± 0.8 | 0.267 ± 0.018 |
| Example 18 | 119.3 ± 1.3 | 0.239 ± 0.011 |
| Example 19 | 127.7 ± 2.1 | 0.204 ± 0.009 |

Figure 1:
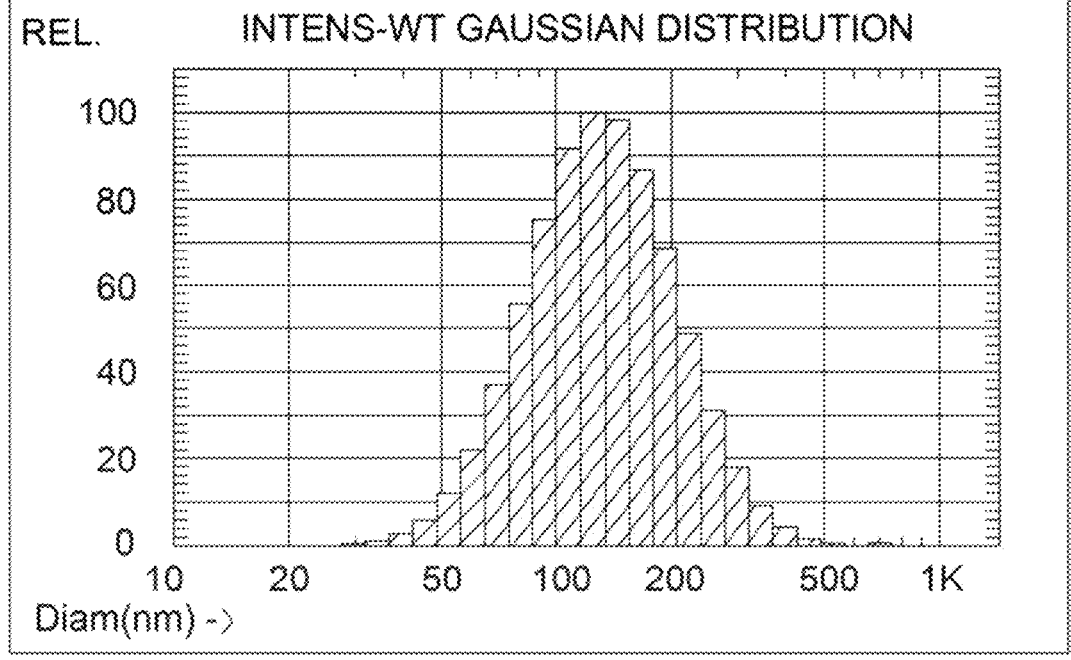
FIG. 1 shows the particle size and distribution diagram of the dual-targeting biomimetic liposome with ELE and CTX prepared in Example 1 of the present disclosure.
Figure 2:
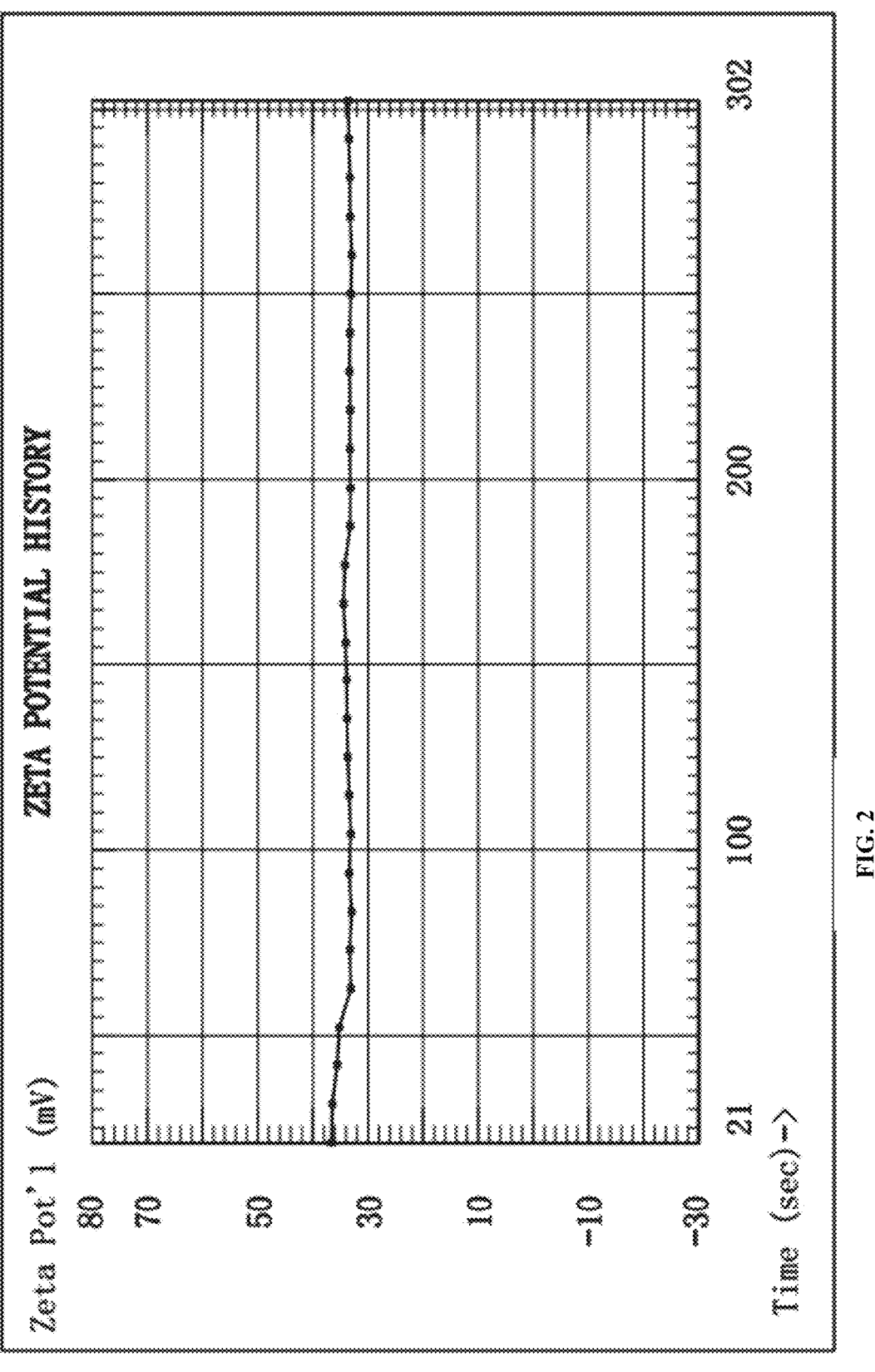
FIG. 2 shows the Zeta potential diagram of the dual-targeting biomimetic liposome with ELE and CTX prepared in Example 1 of the present disclosure.
Figure 3:
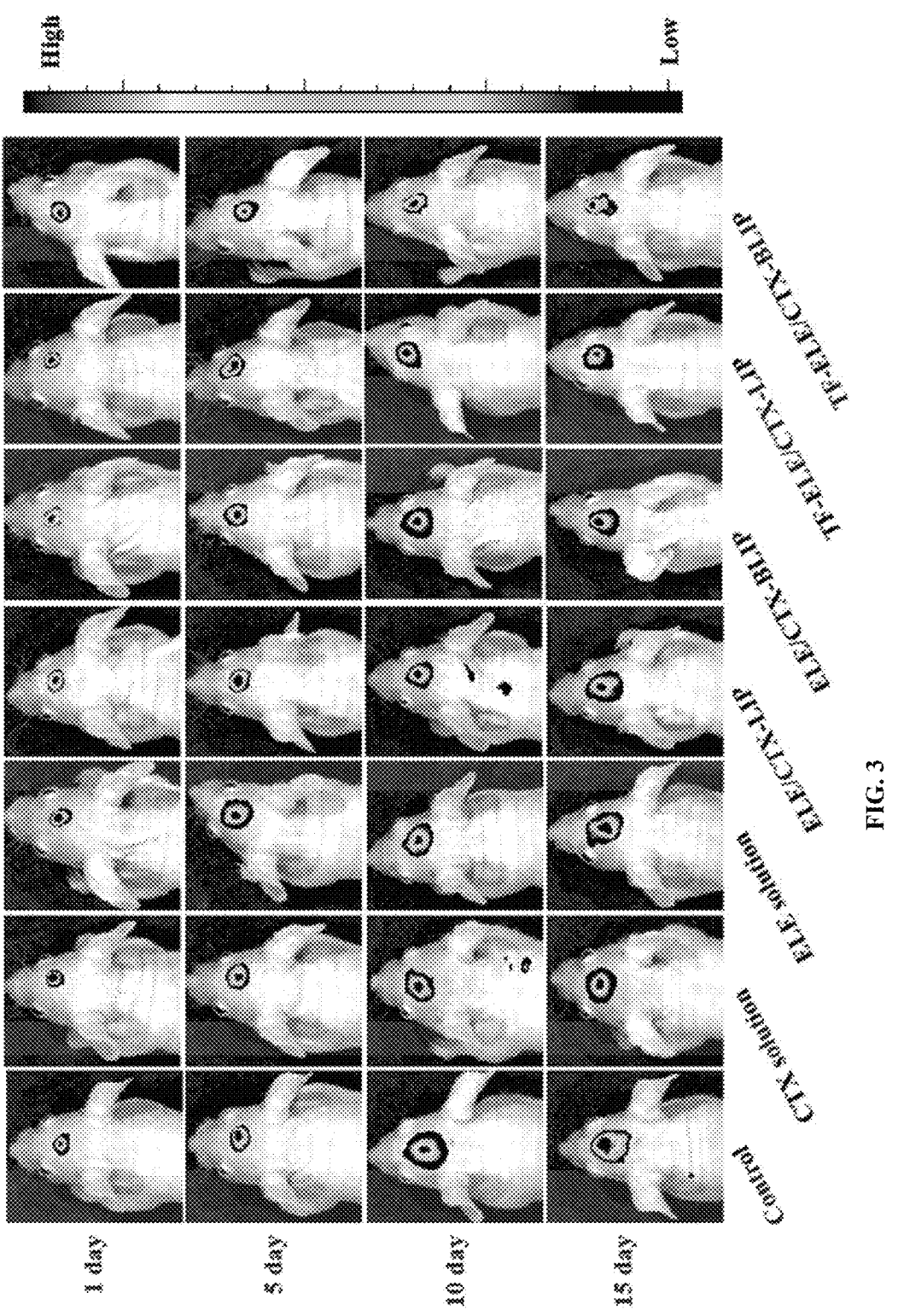
FIG. 3 shows the fluorescence quantification of a tumor tissue after treatment of dual-targeting biomimetic liposome with ELE and CTX prepared in Example 1 of the present disclosure and a control preparation.
Figure 4A:
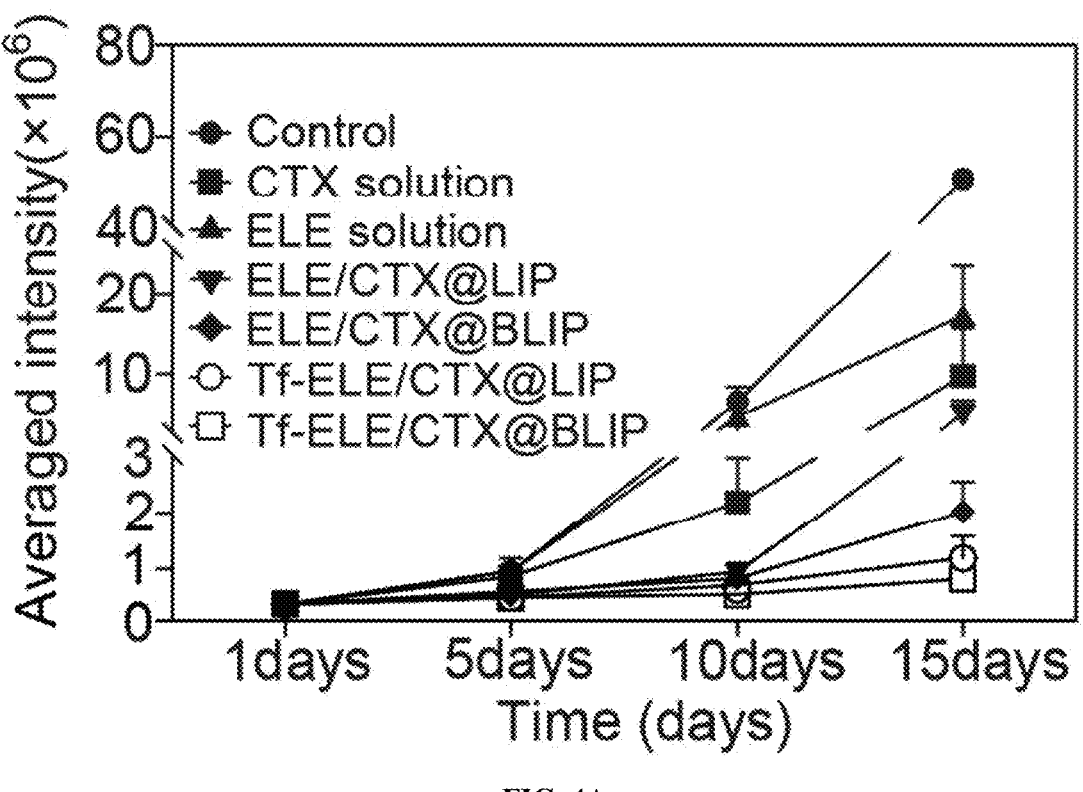
Figure 4B:
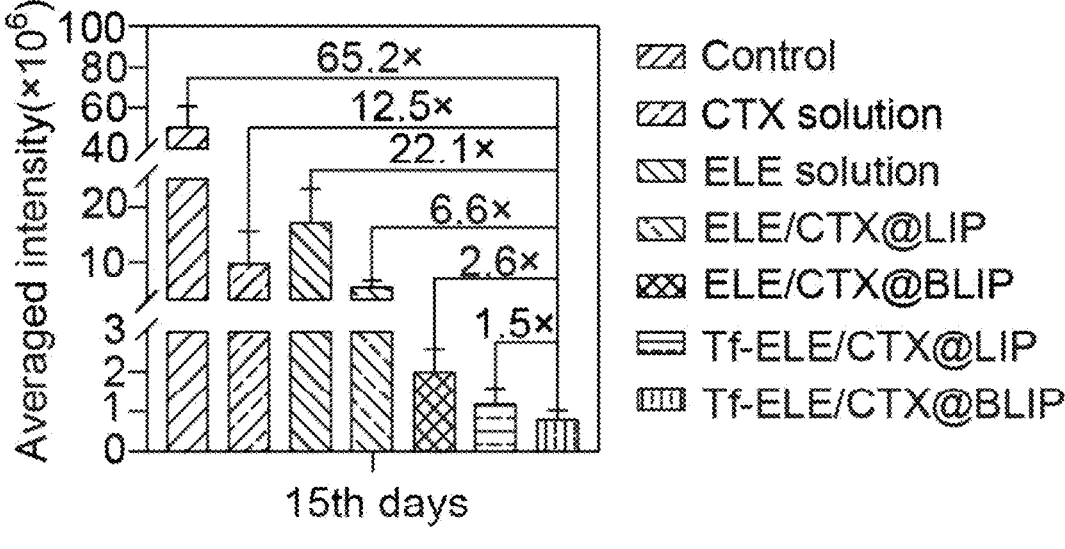
Figure 4C:
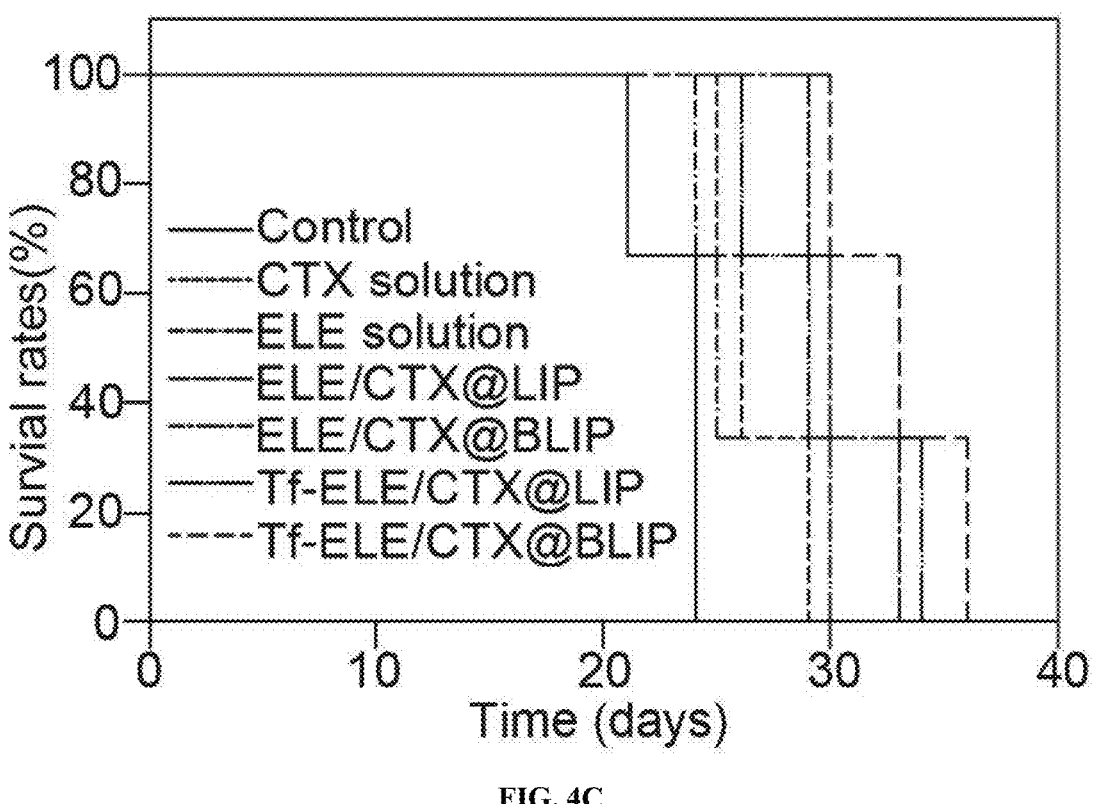
Figure 4D:
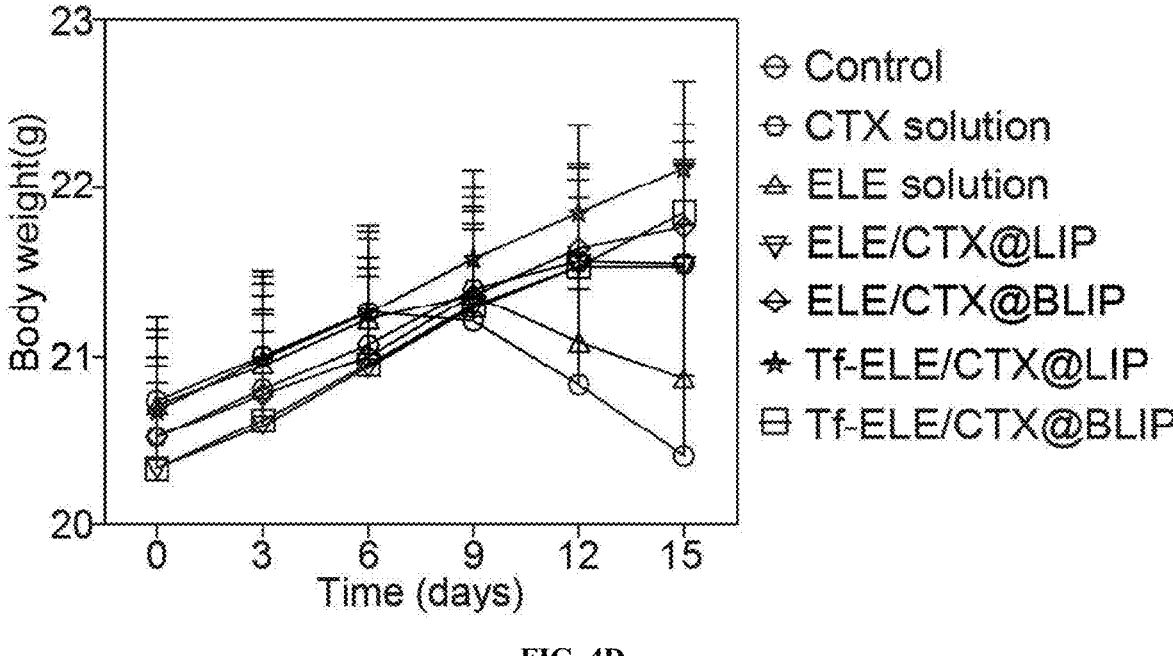
Figure 5A:
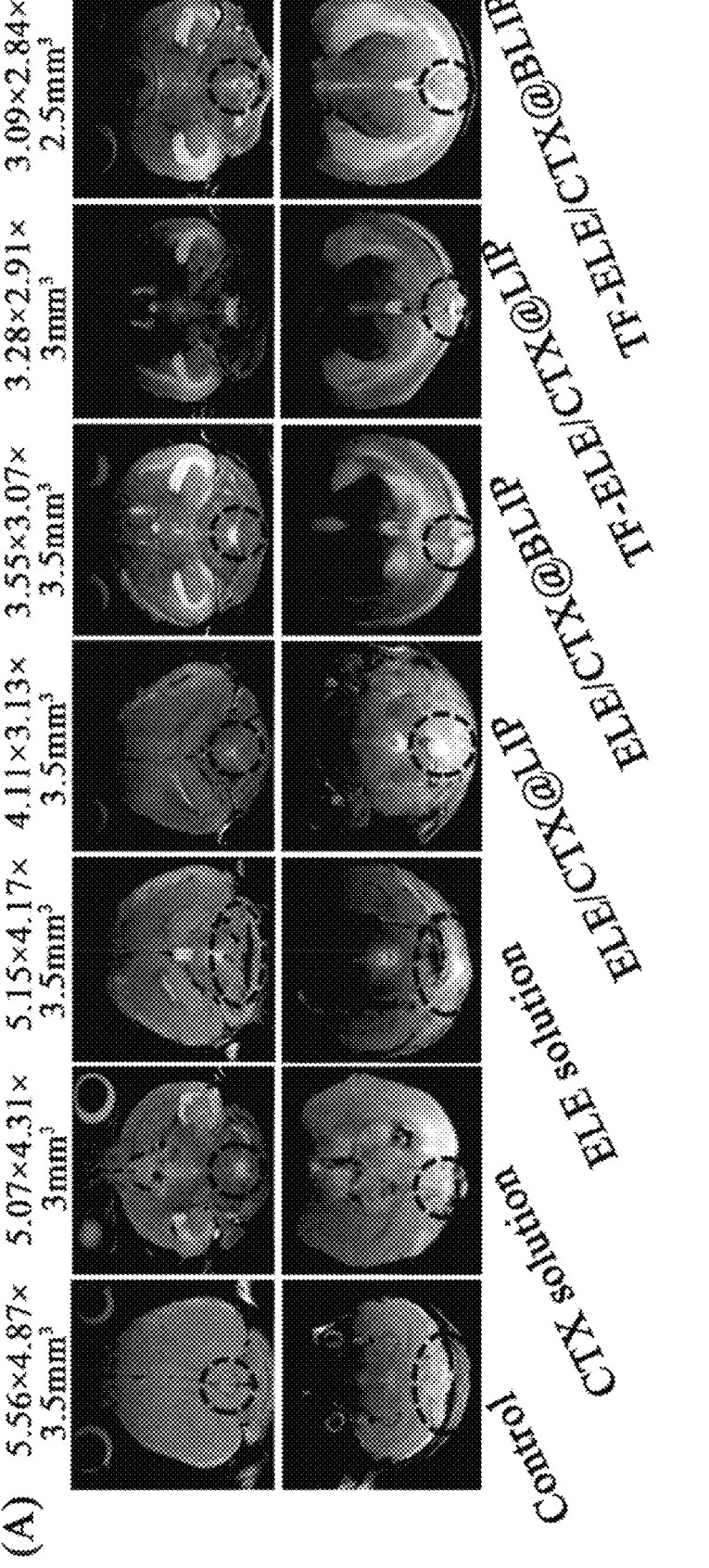
Figure 5B:
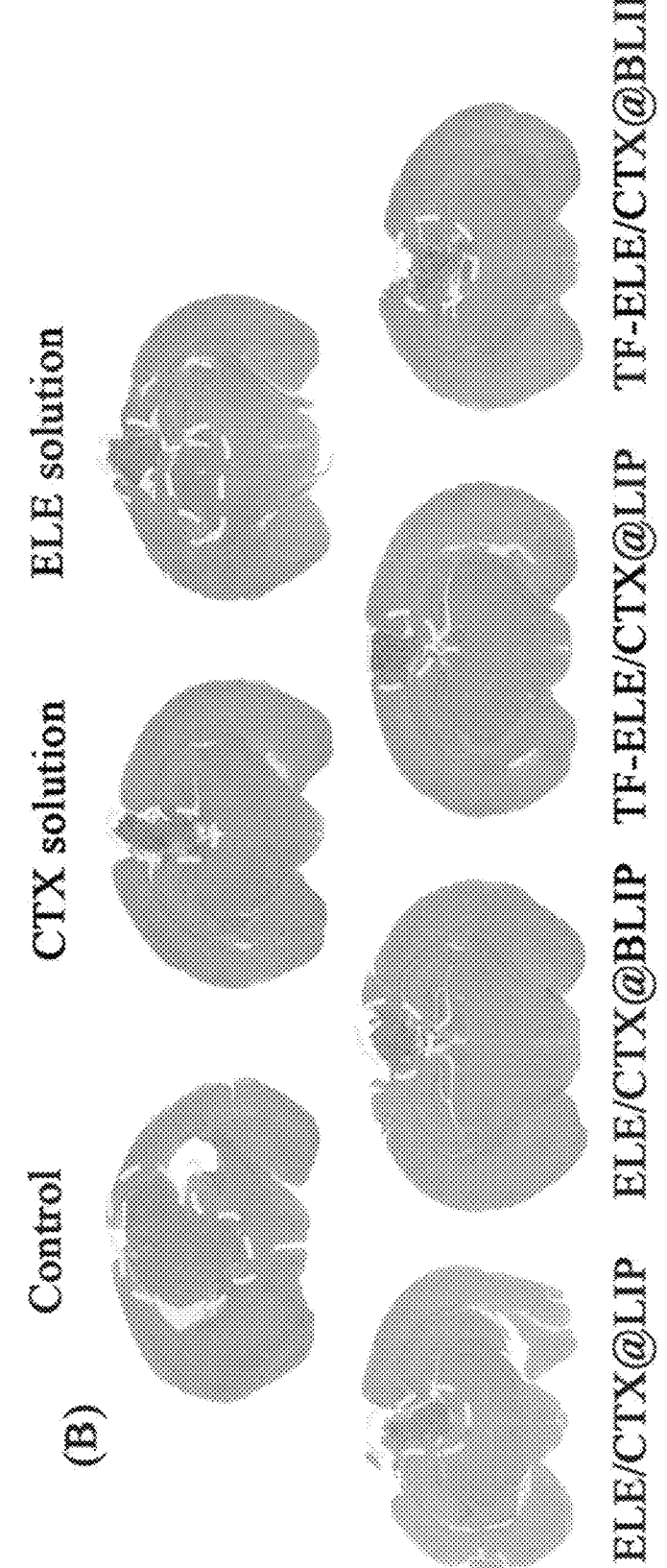
Figure 5C:
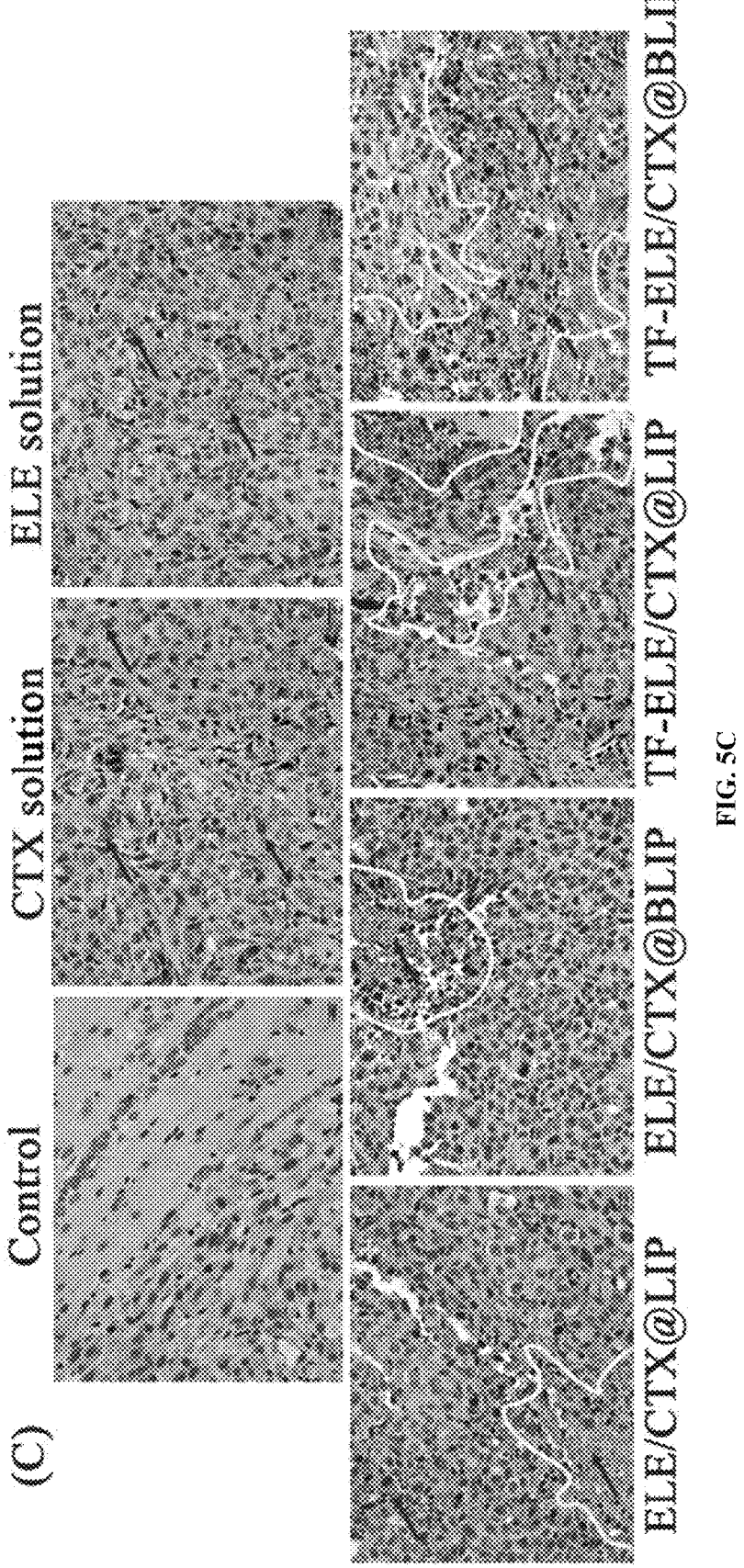
Figure 5D:
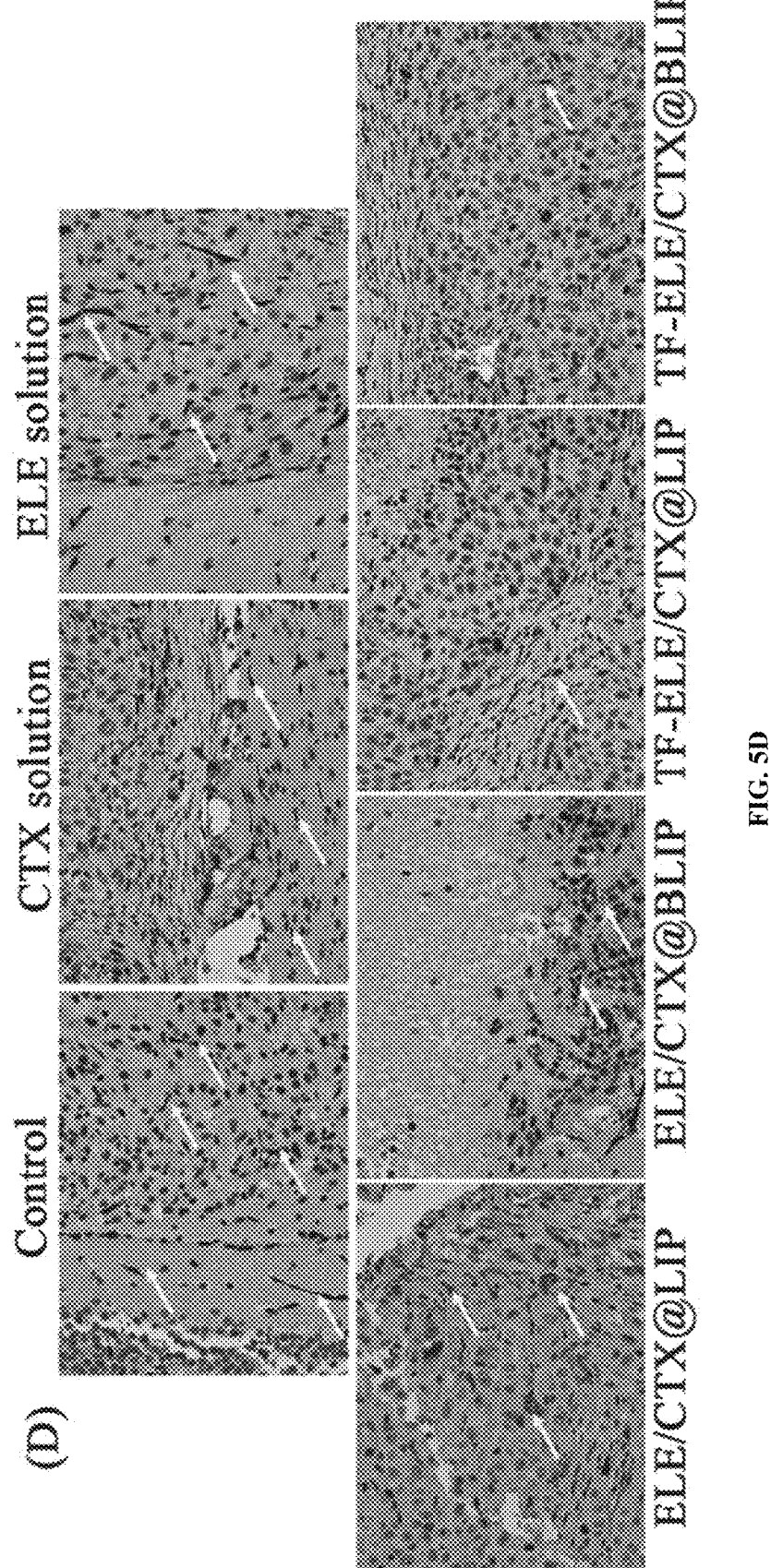

FIG. 1 showed the particle size and distribution diagram of the dual-targeting biomimetic liposome with ELE and CTX prepared in Example 1. As shown in Table 1 and FIG. 1, the dual-targeting biomimetic liposome with ELE and CTX showed moderate particle size and uniform particle size distribution. The Zeta potential value of dual-targeting biomimetic liposome with ELE and CTX prepared in Example 1 was tested, and the results were shown in FIG. 2. As shown in FIG. 2, the absolute value of the Zeta potential of dual-targeting biomimetic liposome with ELE and CTX was greater than 25 mV, reflecting that the preparation had a desirable physical stability.

II. Pharmacodynamics of Dual-Targeting Biomimetic Liposome with ELE and CTX Prepared in Example 1

42 tumor-bearing nude mice were randomly divided into 7 groups, with 6 mice in each group, including: (1) control group, also called Control group (physiological saline); (2) CTX solution group, CTX injection; (3) ELE solution group, ELE injection, 25 mg/kg, once every other day; (4) ELE/CTX@LIP group, ELE/CTX liposome; (5) ELE/CTX@BLIP group, ELE/CTX biomimetic liposome; (6) Tf-ELE/CTX@LIP group, Tf-modified ELE/CTX targeting liposome; (7) Tf-ELE/CTX@BLIP, the dual-targeting biomimetic liposome with ELE and CTX.

Administration was conducted slowly via the tail vein. Tail vein injection was conducted on days 1, 3, 5, 7, 9, and 11. Groups 2, 4, 5, 6, and 7 were given 2.5 mg/kg (CTX) for the first time, and then 0.625 mg/kg for the next 5 times. After different treatments, mice underwent bioluminescence imaging on days 1, 5, 10, and 15 to measure tumor growth. The body weight and survival time of mice were recorded every 3 d. A tumor volume (Vt) was calculated based on the MRI image, Vt=a×b×c/2, where a represented a tumor length, b represented a tumor width, and c represented a height of the magnetic layer (number of layers×thickness of each layer at 0.5 mm).

The results of each treatment group were shown in FIG. 3 to FIGS. 6A-Q. The results showed that after 15 d of treatment, the tumor fluorescence intensity of the Tf-ELE/CTX@BLIP group was the smallest compared with that in other groups. Quantitative analysis showed that Tf-ELE/CTX@BLIP had an inhibitory effect on tumor growth. The tumor fluorescence intensity was 65.2, 12.5, 22.1, 6.6, 2.6, and 1.5 times lower than that of the control group, CTX solution group, ELE solution group, ELE/CTX@LIP group, ELE/CTX@BLIP group, and Tf-ELE/CTX@LIP group, respectively. These results were consistent with the fluorescence images, indicating that Tf-ELE/CTX@BLIP-mediated chemotherapy could significantly inhibit the growth of glioma. In addition, the weight of mice in the control group, CTX injection group, and ELE injection group began to decrease on the 9th day, while the weight of mice in other groups increased significantly within 15 d after treatment. This suggested that drug-loaded liposomes contributed to body weight in mice. The ELE/CTX@LIP group had a median survival time of 28 d, which verified that the treatment effect was better than that of the control group, CTX injection group, and ELE injection group. The median survival times of mice in the ELE/CTX@BLIP group and Tf-ELE/CTX@LIP group were 31 d and 30 d, respectively, indicating that mice treated with CTX injection and traditional liposomes had a prolonged survival time. The results showed that targeting liposome had better anti-glioma effects. The average survival time of the Tf-ELE/CTX@BLIP group was 33 d, which was 6.5% and 10.0% longer than the ELE/CTX@LIP and Tf-ELE/CTX@LIP groups, respectively, indicating that Tf/CMP had made a certain contribution to anti-glioma, brain accumulation, and targeting of drugs for homologous glioma.

Tumor progression was assessed by MRI. The results showed that the tumor area in the Tf-ELE/CTX@BLIP treatment group was smaller than that in the other groups. After inoculation of glioma cells, Tf-ELE/CTX@BLIP had obvious tumor inhibitory activity. Briefly, the brain tissue of glioma-bearing mice in the control group and ELE injection group had irregular isometric T1 lesions mixed with T2 space-occupying lesions, which were surrounded by patchy and macular edema areas. The adjacent brain tissue in mice was compressed by the tumors, causing gliosis and unclear boundaries. The left ventricle of the mice was narrowed with its midline shifted to the left side. The brain damages of mice in the CTX solution group were similar to those of the control group and ELE injection group, but no gliosis was seen. Compared with the control group and ELE injection group, the ELE/CTX@LIP group had the same type of lesions and edema around the lesions. The compression of tumors on adjacent brain tissue narrowed the left ventricle and shifted its midline to the left side. There was no edema around the brain tissue lesions in the ELE/CTX@BLIP group and the TF-ELE/CTX@LIP group, the adjacent brain tissue was not compressed, and the midline was clear. In the mice of the TF-ELE/CTX@BLIP group, the border and midline were clearly visible, there was no edema around the lesions, and there was no tumor compression in adjacent brain tissues, indicating that the invasive growth of tumor cells was significantly inhibited.

The H&E staining results of the brain tissue sections of the Tf-ELE/CTX@BLIP-treated group showed that the tumor tissue in the control group had a dense texture, no obvious apoptotic cells, and no necrotic area in the center. Compared with other groups, the necrotic area was less than ¼ of a total area, which was consistent with the shorter survival time. Mice in the free ELE and CTX solution groups had a reduced tumor volume and low (ELE injection group) or obvious (CTX injection group) number of apoptotic cells, suggesting that ELE and CTX exhibited certain anti-glioma effects. Compared with the free ELE&CTX group, mice in the ELE/CTX@LIP, ELE/CTX@BLIP, and Tf-ELE/CTX@LIP groups had further reductions in glioma volume. The glioma showed a loose texture with obvious apoptotic cells and a central area of necrosis. The necrosis area was close to ½ of the total area, showing a strong anti-glioma effect. In addition, the Tf-ELE/CTX@BLIP group had the smallest glioma volume, and the necrotic area was close to ¾ of the total tumor area, indicating that the active targeting biomimetic nanoplatform had the best anti-glioma effect.

TUNEL staining was conducted on brain tissue to evaluate an ability of the Tf-ELE/CTX@BLIP to induce cell apoptosis. The Tf-ELE/CTX@BLIP treatment group had the highest cell apoptosis rate, which was consistent with the results of the cell apoptosis experiment, indicating that Tf-ELE/CTX@BLIP could promote tumor cell apoptosis in vivo; while the apoptotic activity in the control group was negligible. In addition, the expression of P-gp was also evaluated. Compared with the control group, ELE/CTX solution group, and classic liposomes, Tf-ELE/CTX@BLIP had the lowest expression level of P-gp, suggesting that Tf-ELE/CTX@BLIP could not induce the positive expression of P-gp and could bypass the efflux effect.

III. Comparison of the active targeting and immune evasion capacities of dual-targeting biomimetic liposome with ELE and CTX prepared in Example 1, and the affinity of Tf-ELE/CTX@BLIP to various tumor cells:

Fluorescence-loaded Tf-ELE/CTX@BLIP was incubated with different cell lines, including SPC-A-1 cells (human lung adenocarcinoma cells), A549 cells (lung cancer cells), MDA-MB-231 cells (human breast cancer cells), LM-3 cells (liver cancer cells), U251 cells, C6 cells, and RG2 cells. 30,000 cells (in 2 mL of medium) were inoculated into a 6-well plate. After incubation for 12 h, the cell medium was replaced with fresh medium of Tf-RhoB@BLIP (RhoB=20 µg/mL). After 2 h, trypsin was added to digest and collect the cells. The collected cells were placed in a centrifuge tube with a large amount of PBS and centrifuged, a supernatant was removed, and a large amount of PBS was added again and centrifuged to remove fluorescent substances that might not be engulfed by the cells and to remove the digestive fluid. After washing, 1 mL of PBS was added to form a cell suspension, which was transferred to a flow tube for flow cytometry analysis. Similarly, RG2 cells inoculated into a 6-well plate (3×105 cells/well) were also incubated with ELE/CTX@LIP, ELE/CTX@BLIP, Tf-ELE/CTX@LIP, and Tf-ELE/CTX@BLIP B (RhoB=20 µg/mL) for 2 h. The cells were fixated with 4% paraformaldehyde, stained with DAPI, washed three times with PBS, and finally imaged with a confocal laser scanning microscope and analyzed by flow cytometry. ELE/CTX@LIP, ELE/CTX@BLIP, Tf-ELE/CTX@LIP, and Tf-ELE/CTX@BLIP (Rho B=20 µg/mL) were applied to macrophages RAW264.7 for 2 h, and the cell uptake was detected by CLSM and flow cytometry.

The results were shown in FIGS. 7A-F. The results showed that the fluorescence intensity of Tf-ELE/CTX@BLIP in the RG2 cell group was 1.21 to 2.02 times that of other cell lines. The higher uptake efficiency of RG2 cells confirmed the homologous targeting capacity of Tf-ELE/CTX@BLIP. In addition, laser confocal results showed that after 2 h of exposure at 37° C., more Tf-ELE/CTX@BLIP entered the cytoplasm of RG2 glioma cells, showing a stronger fluorescence signal compared with that of ELE/CTX@LIP, Tf-ELE/CTX@LIP, ELE/CTX@BLIP, and Tf-ELE/CTX@BLIP. This further demonstrated that Tf-ELE/CTX@BLIP had a homologous targeting capacity. Quantitative analysis results of flow cytometry showed that the fluorescence intensity of cells under the action of Tf-ELE/CTX@BLIP was 3.34 to 5.83 times higher that of other groups, showing an excellent active targeting capacity.

In addition, CLSM imaging and flow cytometry were conducted to detect the internalization of Tf-ELE/CTX@BLIP, Tf-ELE/CTX@LIP, ELE/CTX@BLIP, and ELE/CTX@LIP by RAW264.7 macrophages to detect anti-phagocytic properties. The results showed that only an extremely small amount of Tf-ELE, CTX@BLIP, and ELE/CTX@BLIP were phagocytosed by raw RAW264.7 macrophages, with a fluorescence intensity 1.83 to 1.92 times weaker that of Tf-ELE/CTX@LIP- and ELE/CTX@LIP-treated cells. This indicated that the biomimetic liposome had a desirable immune evasion capacity.

IV. Cytotoxicity, Pro-Apoptosis, and P-Gp Inhibitory Effect of Dual-Targeting Biomimetic Liposome with ELE and CTX Prepared in Example 1

The cytotoxicity of ELE/CTX@LIP, ELE/CTX@BLIP, Tf-ELE/CTX@LIP, and Tf-ELE/CTX@BLIP on RG2 cells was separately detected by CCK-8 method. The RG2 cells (3,000 cells/well) were inoculated in a 96-well plate. After 24 h, the cells were treated with ELE/CTX@LIP, ELE/CTX@BLIP, Tf-ELE/CTX@LIP, and Tf-ELE/CTX@ BLIP for 48 h separately (CTX concentration was 0.4 ng/mL to 200 ng/ml). Untreated cells served as a negative control. The medium was used as a blank control to evaluate cytotoxicity. The absorbance at 450 nm was measured using a Spark multifunctional microplate detection platform (Tecan, Switzerland) to quantitatively measure the cell viability.

A number of apoptotic cells was detected by flow cytometry (CytoFLEX S, USA). ELE/CTX@LIP, ELE/CTX@BLIP, Tf-ELE/CTX@LIP, and Tf-ELE/CTX@BLIP were separately incubated for 48 h under the effect equivalent to 50 ng/mL CTX, and then treated with apoptosis detection kit (Genview, USA) for 10 min. The percentage of apoptotic cells was analyzed with a FACS Calibur system. The untreated cells served as a negative control.

The bEnd.3 cell line was cultured as described above. The cells were inoculated into a 6-well plate (5×105 cells/well) and pretreated for 12 h. ELE/CTX@LIP, ELE/CTX@BLIP, Tf-ELE/CTX@LIP, and Tf-ELE/CTX@BLIP (50 ng/mL) were separately treated with verapamil (0.625 µg/mL) for 0.5 h, and then with a P-gp substrate rhodamine 123 (20 µg/mL) for 2 h. The cells were fixated with 4% paraformaldehyde for 30 min, washed 3 times with PBS, and then measured using fluorescence microscopy and flow cytometry.

The results were shown in FIGS. 8A-L. CCK-8 quantitative analysis showed that the ELE/CTX@LIP, ELE/CTX@BLIP, Tf-ELE/CTX@LIP, and Tf-ELE/CTX@BLIP (C CTX 0.4 ng/mL to 200 ng/mL) groups had IC50 values of 54.25±4.90 ng/ml, 42.70±0.76 ng/mL, 31.30±1.44 ng/ml, and 27.38±0.67 ng/mL, respectively. Meanwhile, the Tf-ELE/CTX@BLIP, Tf-ELE/CTX@LIP, ELE/CTX@BLIP, and ELE/CTX@LIP (C CTX=50 ng/mL) had cell inhibition rates of 56.50%±0.86%, 54.69%±1.79%, 52.41%±1.50%, and 49.44%±1.33%, respectively. The Tf-ELE/CTX@BLIP showed a high cytotoxicity to RG2 cells, indicating its potential advantages for in vivo applications.

Annexin V-FITC/PI double staining assay showed that compared with the control group (25.68%), the number of apoptosis in RG2 cells exposed to CTX injection group (42.47%), ELE+CTX group (67.89%), Tf-ELE/CTX@BLIP group (60.97%), ELE/CTX@BLIP group (56.02%), Tf-ELE/CTX@LIP group (60.80%), and ELE/CTX@LIP group (42.49%) increased significantly. This indicated that ELE+CTX could inhibit glioma cell proliferation by activating apoptosis channels; while Tf-ELE/CTX@BLIP coupled to Tf and embedded in CMP through liposomes could enhance the pro-apoptotic effect, which was consistent with that in the cytotoxicity experiment.

To study the transport of Tf-modified liposomes across the BBB, the accumulation of rhodamine-123 in bEnd.3 was examined. P-gp is one of the main physiological disorders of the BBB (efflux effect). Verapamil, a P-gp efflux inhibitor, was used as a positive control, and a fluorescent substrate rhodamine 123 of P-gp was used to study the efflux effect. The results showed that after incubation with Tf-ELE/CTX@LIP and Tf-ELE/CTX@BLIP, the efflux of rhodamine-123 from bEnd.3 was significantly reduced compared with that in the control group. This indicated that Tf-ELE/CTX@BLIP and Tf-ELE/CTX@LIP could significantly increase the permeability of rhodamine-123 across the BBB. Quantitative analysis by flow cytometry showed that the fluorescence intensity of cells treated with Tf-ELE/CTX@BLIP and Tf-ELE/CTX@LIP increased significantly, indicating the inhibition of efflux effect.

In summary, the dual-targeting biomimetic liposome with ELE and CTX had a desirable efficacy against brain glioma. Compared with ELE injection, CTX injection, and traditional liposomes, the product of the present disclosure shows greater advantages and was better in efficacy and safety. Encapsulating the ELE and CTX in a flexible liposome allows the above two drugs to act synergistically on tumor cells. By adding a certain amount of the ELE and improving the preparation, a dosage of CTX is significantly reduced while an efficacy is enhanced, such that toxic and side effects of CTX are reduced to improve safety. Therefore, the dual-targeting biomimetic liposome has desirable clinical translation application prospects for glioma.

The above embodiments are only preferred ones of the present disclosure, and are not intended to limit the present disclosure in any form. Although the present disclosure has been disclosed by the foregoing embodiments, these embodiments are not intended to limit the present disclosure. Any person skilled in the art may make some changes or modifications to implement equivalent embodiments with equivalent changes by using the technical contents disclosed above without departing from the scope of the technical solution of the present disclosure. Any simple modification, equivalent change and modification made to the foregoing embodiments according to the technical essence of the present disclosure without departing from the content of the technical solution of the present disclosure shall fall within the scope of the technical solution of the present disclosure.

What is claimed is:

1. A dual-targeting biomimetic liposome with elemene (ELE) and cabazitaxel (CTX), wherein each 100 mL of the dual-targeting biomimetic liposome with ELE and CTX comprises 0.15 g to 0.75 g of the ELE, 0.5 mL to 2.5 mL of absolute ethanol, 0.015 g to 0.07 g of the CTX, 0.25 g to 1 g of oil, 0.25 g to 1 g of a polyethylene glycol (PEG) derivative, 1 g to 5 g of a phospholipid, 0.05 g to 0.2 g of cholesterol, 0.025 g to 0.1 g of distearoyl phosphatidylethanolamine-polyethylene glycol-transferrin (DSPE-PEG-Tf), 0.005 g to 0.025 g of a tumor cell membrane protein (CMP), and water as a balance.

2. The dual-targeting biomimetic liposome with ELE and CTX according to claim 1, wherein the oil is one or more selected from the group consisting of medium-chain triglyceride (MCT), soybean oil, palm oil, coconut oil, fish oil, hydrogenated oil, and animal oil.

3. The dual-targeting biomimetic liposome with ELE and CTX according to claim 1, wherein the phospholipid is one or more selected from the group consisting of soybean phospholipid, egg yolk phospholipid, hydrogenated phospholipid, and synthetic phospholipid.

4. The dual-targeting biomimetic liposome with ELE and CTX according to claim 1, wherein the PEG derivative is selected from the group consisting of D-$\alpha$-tocopherol polyethylene glycol succinate (TPGS) and DSPE-PEG.

5. The dual-targeting biomimetic liposome with ELE and CTX according to claim 1, wherein the DSPE-PEG-Tf is selected from the group consisting of DSPE-PEG2000-Tf, DSPE-PEG3000-Tf, DSPE-PEG4000-Tf, and DSPE-PEG5000-Tf.

6. The dual-targeting biomimetic liposome with ELE and CTX according to claim 1, further comprising an osmotic pressure regulator.

7. The dual-targeting biomimetic liposome with ELE and CTX according to claim 6, wherein the osmotic pressure regulator is one or more selected from the group consisting of glycerol, glucose, sucrose, trehalose, maltose, and mannitol.

8. The dual-targeting biomimetic liposome with ELE and CTX according to claim 1, wherein the ELE and the CTX are at a mass ratio of 10:1.

* * * * *